(12) United States Patent
Cinbis et al.

(10) Patent No.: US 9,999,774 B2
(45) Date of Patent: Jun. 19, 2018

(54) OPTICAL TRIGGER FOR THERAPY DELIVERY

(71) Applicant: Medtronic, Inc., Minneapolis, MN (US)

(72) Inventors: Can Cinbis, Salt Lake City, UT (US); Jonathan L. Kuhn, Ham Lake, MN (US); Richard J O'Brien, Hugo, MN (US); James K Carney, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 90 days.

(21) Appl. No.: 14/695,013

(22) Filed: Apr. 23, 2015

(65) Prior Publication Data

US 2015/0321012 A1    Nov. 12, 2015

Related U.S. Application Data

(60) Provisional application No. 61/989,114, filed on May 6, 2014.

(51) Int. Cl.
| | | |
|---|---|---|
| *A61N 1/00* | (2006.01) | |
| *A61N 1/365* | (2006.01) | |
| *A61N 1/39* | (2006.01) | |
| *A61N 1/372* | (2006.01) | |
| *A61N 1/375* | (2006.01) | |
| *H04B 10/80* | (2013.01) | |

(52) U.S. Cl.
CPC ....... *A61N 1/36514* (2013.01); *A61N 1/3756* (2013.01); *A61N 1/37205* (2013.01); *A61N 1/37288* (2013.01); *A61N 1/3987* (2013.01); *H04B 10/802* (2013.01)

(58) Field of Classification Search
CPC ............ A61N 1/36514; A61N 1/37205; A61N 1/37288; A61N 1/3756; A61N 1/3987; H04B 10/802
See application file for complete search history.

(56) References Cited

U.S. PATENT DOCUMENTS

| | | |
|---|---|---|
| 4,481,950 A | 11/1984 | Duggan |
| 4,543,955 A | 10/1985 | Schroeppel |
| 5,354,316 A | 10/1994 | Keimel |
| 5,545,186 A | 8/1996 | Olson et al. |
| 5,855,593 A | 1/1999 | Olson et al. |
| 5,902,326 A | 5/1999 | Lessar et al. |
| 6,393,316 B1 | 5/2002 | Gillberg et al. |
| 6,592,519 B1 | 7/2003 | Martinez |
| 6,711,440 B2 * | 3/2004 | Deal ............... A61N 1/372 607/9 |

(Continued)

OTHER PUBLICATIONS (PCT/US2015/029495) PCT Notification of Transmittal of the International Search Report and the Written Opinion of the International Searching Authority, dated Aug. 12, 2015, 9 pages.

*Primary Examiner* — Lindsey G Wehrheim

(57) ABSTRACT

A medical device system is configured to sense a physiological signal by a first device and generate a control signal by the first device in response to the physiological signal. An optical transducer is controlled by the first device to emit an optical trigger signal in response to the control signal. A second device receives the optical trigger signal and delivers an automatic therapy to a patient in response to detecting the optical trigger signal.

25 Claims, 14 Drawing Sheets

(56) References Cited

U.S. PATENT DOCUMENTS

| | | |
|---|---|---|
| 7,742,812 B2 | 6/2010 | Ghanem et al. |
| 7,904,153 B2 | 3/2011 | Greenhut et al. |
| 8,160,684 B2 | 4/2012 | Ghanem et al. |
| 8,275,432 B2 | 9/2012 | Kuhn et al. |
| 8,433,409 B2 | 4/2013 | Johnson et al. |
| 8,452,402 B2 | 5/2013 | Ecker et al. |
| 8,532,785 B1 | 9/2013 | Crutchfield et al. |
| 8,541,131 B2 | 9/2013 | Lund et al. |
| 8,666,505 B2 | 3/2014 | O'Brien et al. |
| 2005/0043761 A1 | 2/2005 | Connelly et al. |
| 2008/0077190 A1* | 3/2008 | Kane .................. A61N 1/3752 607/37 |
| 2008/0119911 A1 | 5/2008 | Rosero |
| 2008/0288039 A1 | 11/2008 | Reddy |
| 2009/0326356 A1* | 12/2009 | Kracker ............... A61B 5/0006 600/363 |
| 2010/0106210 A1 | 4/2010 | Hedberg et al. |
| 2010/0114221 A1* | 5/2010 | Krause ............... A61N 1/36114 607/7 |
| 2011/0125078 A1 | 5/2011 | Denison et al. |
| 2012/0172892 A1 | 7/2012 | Grubac et al. |
| 2013/0116738 A1 | 5/2013 | Samade et al. |
| 2013/0138006 A1 | 5/2013 | Bornzin et al. |

* cited by examiner

OPTICAL TRIGGER FOR THERAPY DELIVERY

REFERENCE TO RELATED APPLICATIONS

This application claims priority to U.S. Pat. Application No. 61/989,114 filed provisionally on May 6, 2014 and incorporated herein by reference in its entirety. This application also cross-references U.S. Pat. Application No. 61/989,123 and U.S. Pat. Application No. 61/989,302, filed provisionally on May 6, 2014; and U.S. Pat. No. 9,492,671 (Carney, et al) and U.S. Pat. No. 9,669,224 (Carney, et al), filed on even date herewith, all of which are incorporated herein by reference in their entirety.

TECHNICAL FIELD

The disclosure relates to an implantable medical device system and associated method for delivering a therapy using an optically-triggered therapy delivery device.

BACKGROUND

Implantable pacemakers and cardioverter defibrillators (ICDs) are available for delivering electrical stimulation therapies to a patient's heart, such as bradycardia pacing, cardiac resynchronization therapy (CRT), anti-tachycardia pacing and cardioversion/defibrillation shocks. Medical device technology advancement has led toward smaller and smaller implantable devices. Recently, leadless intracardiac pacemakers have been introduced which can be implanted directly in a heart chamber. Elimination of transvenous, intracardiac leads has several advantages. For example, complications due to infection associated with a lead extending from a subcutaneous pacemaker pocket transvenously into the heart can be eliminated. Other complications such as "twiddler's syndrome", lead fracture or poor connection of the lead to the pacemaker are eliminated in the use of an intracardiac pacemaker having no transvenous leads.

New challenges arise, however, in controlling an intracardiac pacemaker to deliver pacing pulses in synchrony with paced or sensed events occurring in other heart chambers. Cardiac resynchronization therapy (CRT) is an example of a pacing therapy that includes delivering pacing pulses in a heart chamber at a predetermined time interval after a sensed or paced event in another heart chamber. CRT is a treatment for heart failure patients in which one or more heart chambers are electrically paced to restore or improve heart chamber synchrony. Improved heart chamber synchrony is expected to alleviate symptoms of heart failure. Achieving a positive clinical benefit from CRT, however, may be dependent on several therapy control parameters, such as the timing intervals used to control pacing pulse delivery, e.g. an atrio-ventricular (AV) interval and/or an inter-ventricular (VV) interval. The AV interval controls the timing of ventricular pacing pulses relative to an atrial depolarization, intrinsic or paced. The VV interval controls the timing of a pacing pulse in one ventricle relative to a paced or intrinsic sensed event in the other ventricle. Pacing may be delivered in the right ventricle (RV) and/or the left ventricle (LV) to restore ventricular synchrony.

SUMMARY

In general, the disclosure is directed to an implantable medical device (IMD) system including a therapy delivery device and a sensing device and an associated method for triggering the therapy delivery device to deliver therapy. The sensing device senses a physiological signal to determine a need for therapy and generates a control signal passed to an optical emitting device when therapy delivery by the therapy delivery device is required. The optical emitting device emits an optical trigger signal that is detected by the therapy delivery device. In response to detecting the trigger signal, the therapy delivery device delivers at least a portion of a therapy.

In one example, the disclosure provides a medical device system for automatically delivering a therapy comprising a first device configured to sense a physiological signal and generate a control signal in response to the physiological signal, an optical emitting device controlled by the first device to emit an optical trigger signal in response to receiving the control signal from the first device, and a second device comprising a light detector for receiving the optical trigger signal. The second device is configured to detect the optical trigger signal and deliver a therapy to a patient in response to detecting the optical trigger signal.

In another example, the disclosure provides a method for delivering an automatic therapy by a medical device system. The method includes sensing a physiological signal by a first device, generating a control signal by the first device in response to the physiological signal, controlling an optical emitting device to emit an optical trigger signal in response to the control signal, detecting the optical trigger signal by a second device comprising a light detector, and delivering the therapy to a patient in response to the light detector detecting the optical trigger signal.

In yet another example, the disclosure provides a non-transitory computer readable storage medium storing a set of instructions that cause an implantable medical device system to sense a physiological signal by a first device, generate a control signal by the first device in response to the physiological signal, control an optical emitting device to emit an optical trigger signal in response to the control signal, detect the optical trigger signal by a second device comprising a light detector; and deliver a therapy to a patient in response to the light detector detecting the optical trigger signal.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1A:
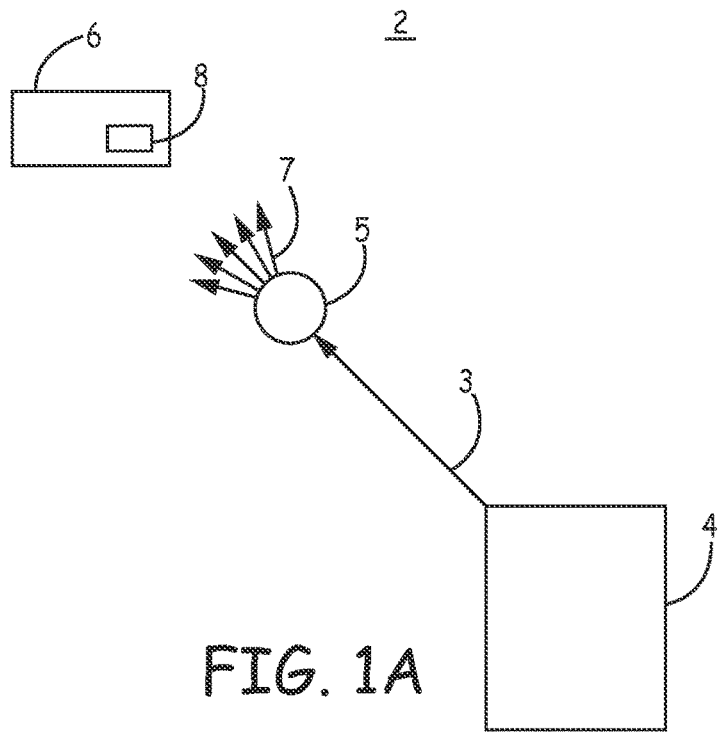
FIG. 1A is a conceptual diagram of an implantable medical device (IMD) system including an optically-triggered therapy delivery device.

IMD systems and associated techniques are disclosed herein for sensing physiological signals using a sensing device implanted at one location and triggering a therapy delivery device to deliver an automatic therapy to a targeted patient tissue at a second location. The therapy delivery device is triggered to deliver the therapy by an optical trigger signal transmitted by a light emitting device that is controlled by the sensing device. Automatic therapy delivery is achieved by the separate sensing and therapy delivery devices without requiring the two devices to be physically connected to each other. Among other things, elimination of the physical connection between the sensing and therapy delivery components of an IMD system enables minimally invasive implant procedures to be used, down-sizing of IMD system components, and/or elimination of some components such as medical leads sensing capability in the therapy delivery device, and a radio frequency (RF) amplifier and transceiver in the therapy delivery device.

As used herein, an "optical trigger signal" is an optical signal emitted by an optical transducer when an electrical control signal is applied to the transducer. The optical trigger signal is a command signal, which is generated by and sent from the sensing device to the therapy delivery device via an emitting device using optical energy as a means for communication. An optical trigger signal as used herein is not a physiological signal, such as blood oxygen saturation signal, that may be sensed by an optical sensor that emits and collects light for measuring a physiological parameter for determining if a therapy is needed. Rather the optical trigger signal is a device-generated control signal that is emitted after a decision has already been made that a therapy is needed. The optical trigger signal is a control signal that is used to control the timing of the therapy.

A "triggered therapy delivery device" as used herein is a device that is triggered by the optical trigger signal to deliver a therapy to a targeted patient tissue. In the illustrative embodiments described herein, the therapy is an electrical stimulation therapy, such as a cardiac pacing pulse, though other types of therapy, such as drug delivery, are contemplated.

The triggered therapy delivery device includes a transducer or photosensitive component that produces an electrical signal in response to being subjected to the optical trigger signal. The electrical signal is compared to a trigger signal detection threshold and causes the therapy delivery device to deliver a therapeutic stimulation pulse (or other therapy) to a targeted tissue of the patient when the detection threshold is exceeded. The "triggered therapy delivery device" as disclosed herein, therefore, is not making a decision to deliver therapy based on processing or analysis of a physiological signal sensed using an optical transducer, such as a blood oxygen saturation signal or other a time-varying optical signal that is measured to detect a physiological event or condition. The decision to deliver therapy is made by the sensing device that is controlling the emitting device to emit the optical trigger signal. The sensing device and the therapy delivery device need not be in wired connection with each other.

FIG. 1 is a conceptual diagram of an IMD system 2 including an optically-triggered therapy delivery device. System 2 includes a sensing device 4, an optical emitting device 5, and a therapy delivery device 6. Sensing device 4 is capable of sensing a physiological signal for determining when a therapy is needed. Sensing device 4 may or may not be capable of delivering a therapy directly to the patient. Sensing device 4 is at least capable of sensing a physiological signal, determining need for therapy based on the physiological signal, and producing a control signal 3 passed to emitting device 5. In various examples, sensing device 4 may be a pacemaker, ICD, ECG monitor, hemodynamic monitor, neurostimulator, drug pump, or other IMD.

Sensing device 4 is in wired or wireless communication with optical emitting device 5. Sensing device 4 sends a control signal 3 to emitting device 5 to cause emitting device 5 to emit an optical signal 7. In the diagram, emitting device 5 is shown as a separate device from sensing device 4, however in some examples emitting device 5 is incorporated in sensing device 4. In some applications, sensing device 4 incorporating emitting device 5 may be implanted (or located externally) at a location that is within an optical trigger signal receiving range of therapy delivery device 6. In other applications, the physical locations of sensing device 4 and therapy delivery device 6 may be too far apart or separated by highly reflective tissues or light attenuating anatomical structures that would prohibit reliable reception of an optical trigger signal by therapy delivery device 6 from sensing device 4. In these situations, the emitting device 5 is located at a spaced apart location from sensing device 4 and is positioned to reliably transmit the optical trigger signal to the therapy delivery device 6.

In various embodiments, sensing device 4 may sense any physiological signal or combination of physiological signals used in a particular application for determining a need for therapy. Such signals may include, but are not limited to, an electrical signal such as an ECG (electrocardiogram), EGM (cardiac electrogram), EMG (electromyogram), EEG (electroencephalogram), or nerve action potentials. Additionally or alternatively, sensing device 4 may be configured to sense a mechanical or chemical physiological signal. Other physiological signals that may be sensed by sensing device 4 include, without limitation, a blood or other pressure signal, an optical signal such as an optical signal used to determine blood or tissue oxygen saturation, an acoustical signal such as heart sounds, an activity signal, or a posture signal.

The physiological signals may be used to control the time that therapy delivery device 6 is triggered to deliver therapy relative to sensed physiological events and/or determine a need for therapy delivery based on a state or condition determined from the physiological signal(s) sensed by sensing device 4. As such, sensing device 4 is configured to determine a time that therapy is needed according to a programmed therapy delivery algorithm and therapy delivery control parameters for a given application.

When sensing device 4 determines that it is time for a therapy to be delivered, a control signal 3 is passed to optical emitting device 5. Emitting device 5 may be physically coupled to sensing device 4 by a medical lead for passing the control signal 3 as an electrical signal to emitting device 5. Alternatively, emitting device 5 may be configured to receive wireless telemetry communication signals from sensing device 4, such as a radio frequency (RF) command signal that causes emitting device 5 to emit optical trigger signal 7.

Therapy delivery device 6 includes a light detector 8, which may include an optically conductive window and a photodetector or other light detecting component. In response to detecting the optical trigger signal 7, therapy delivery device 6 delivers a therapy, such as one or more electrical stimulation pulses.

Therapy delivery device 6 is generally a miniaturized device that is adapted for implantation at a targeted therapy delivery site. In some applications, the target therapy delivery site requires a minimized device size in order to avoid complications, minimize patient discomfort, and/or facilitate minimally invasive implantation procedures. As such, therapy delivery device 6 may have reduced functionality for sensing physiological signals, data collection, RF or other telemetry communication, or other functions that may normally be present in a pacemaker, ICD, neurostimulators or other types of IMDs configured to automatically deliver a therapy to a patient.

For example, therapy delivery device 6 may be a transcatheter pulse generator having electrodes positioned along the housing of the device 6. In other examples, a short lead carrying one or more electrodes may extend from device 6. In illustrative embodiments described in greater detail below, the therapy delivery device 6 is a transcatheter intracardiac pacemaker that is triggered by an optical signal from emitting device 5 to deliver one or more cardiac pacing pulses. As used herein, a "transcatheter" pacemaker (or other transcatheter device) is a device that can be implanted at a target location via a catheter or other elongated, tubular delivery tool to advance the device to a target location without necessarily having direct line of sight at the target location. Therapy delivery device 6 is not limited to being a cardiac pacemaker. Device 6 may be embodied as other types of electrical stimulation therapy delivery devices, such as devices configured for delivering electrical stimulation to any excitable tissue, including the central nervous system, peripheral nervous system, smooth muscle tissue and/or skeletal muscle tissue.

Furthermore, it is recognized that a therapy delivery device 6 triggered by optical trigger signal 7 to deliver therapy is not limited to being an electrical stimulation therapy delivery device. In alternative embodiments, therapy delivery device 6 may be configured to deliver other types of therapies using mechanical, optical, pharmaceutical or other therapeutic means. For example, therapy delivery device 6 may be a fluid delivery device for delivering a drug or biological agent.

Figure 1B:
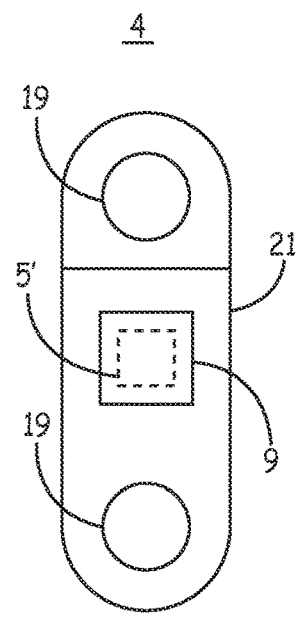
FIG. 1B is a conceptual diagram of a sensing device that may be included in an IMD system for triggering an optically-triggered therapy delivery device.

FIG. 1B is a conceptual diagram of one example of sensing device 4 that may be included in the IMD system 2 of FIG. 1A for triggering an optically-triggered therapy delivery device 6. The sensing device 4 may or may not include therapy delivery capabilities. In the example of FIG. 1B, sensing device 4 is a sensing-only device that sends optical trigger signals to therapy delivery device 6 to achieve therapy delivery. A "sensing-only" device is a device that senses one or more physiological signals to determine a need for therapy but does not deliver therapy directly to a targeted patient tissue.

Sensing device 4 may include a pair of sensing electrodes 19 along uninsulated portions of a conductive housing 21. Emitting device 5' is provided as a housing-based emitting device that is positioned within housing 21 along an optical window 9. Emitting device 5' may include one or more optical transducers for transmitting a trigger signal through window 9 and adjacent tissue to therapy delivery device 6. The window 9 is sealed within an opening of housing 21 and configured to efficiently couple an emitted optical signal from emitting device 5 to adjacent tissue.

In one example, sensing device 4 may be positioned subcutaneously in a parasternal location for sensing ECG signals of a patient's heart. Therapy delivery device 6 may be an intracardiac pacemaker implanted in a heart chamber. Sensing device 4 transmits optical trigger signals from emitting device 5' to therapy delivery device 6 to trigger therapy delivery device 6 to deliver one or more pacing pulses. In this way, a leadless cardiac pacing system is provided including two minimally sized implantable devices.

Figure 2A:
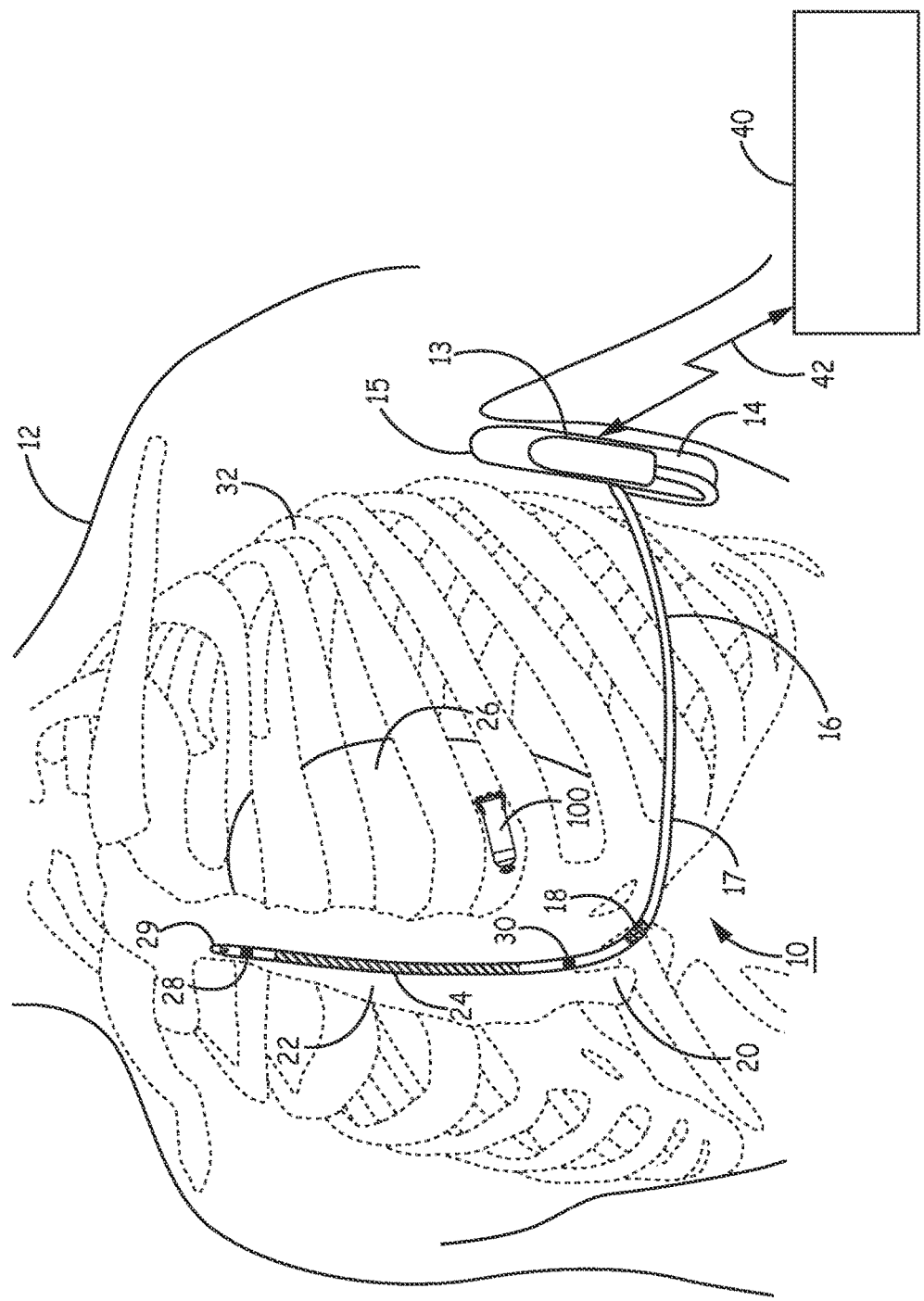
FIG. 2A is a conceptual diagram illustrating an IMD system that may be used to sense cardiac electrical signals in a patient and provide therapy to the patient's heart.

FIG. 2A is a conceptual diagram illustrating an implantable medical device (IMD) system 10 that may be used to sense cardiac electrical signals in patient 12 and provide therapy to heart 26. IMD system 10 includes an intracardiac pacemaker 100 and an ICD 14 coupled to an extravascular defibrillation lead 16. Defibrillation lead 16 includes a defibrillation electrode 24, which may be an elongated coil electrode, a pair of sensing electrodes 28 and 30, illustrated as ring electrodes but may be or other types of electrodes, and an optical signal emitting device 18. Optical signal emitting device 18 includes an optical transducer that is controlled by ICD 14 to emit optical trigger signals to cause pacemaker 100 to deliver one or more pacing pulses.

ICD 14 is shown implanted subcutaneously on the left side of patient 12. Defibrillation lead 16, which is connected to ICD 14, extends medially from ICD 14 toward sternum 22 and xiphoid process 20 of patient 12. At a location near xiphoid process 20 defibrillation lead 16 bends or turns and extends subcutaneously superior, substantially parallel to sternum 22. Defibrillation lead 16 may be implanted such that lead 16 is offset laterally to the left or right side of the body of sternum 22 and may be implanted subcutaneously, e.g., between the skin and the ribs or sternum. Defibrillation lead 16 may be implanted at other locations or angles relative to sternum 22 or positioned further superior or inferior depending on the location of ICD 14, position of electrodes 24, 28, and 30 and optical signal emitting device 18 along lead 16 and the location of pacemaker 100, or other factors. In other instances, lead 16 may be implanted at other extravascular locations. In one example, lead 16 may be implanted at least partially in a substernal location or within ribcage 32, within the thoracic cavity and within or outside the pericardium, not necessarily in direct contact with heart 26.

Defibrillation lead 16 is positioned such that a therapy vector between defibrillation electrode 24 and a second electrode (such as a portion of the housing 15 of ICD 14 or an electrode placed on a second lead) is substantially across one or both ventricles of heart 26. The therapy vector may, in one example, be viewed as a line that extends from a point on the defibrillation electrode 24 to a point on the housing 15 (sometimes referred to as a "can" electrode) of ICD 14. In another example, defibrillation lead 16 may be placed along sternum 22 such that a therapy vector between defibrillation electrode 18 and housing 15 (or other electrode) is substantially across an atrium of heart 26. In this case, system 10 may be used to provide atrial therapies, such as therapies to treat atrial fibrillation.

Optical signal emitting device 18 is positioned to establish an optical signal transmission pathway that does not excessively attenuate the optical trigger signal transmitted from emitting device 18 to a receiver or detector included in intracardiac pacemaker 100. For example, the location of emitting device 18 may be selected so that a direct optical pathway between emitting device 18 and pacemaker 100 avoids highly reflective or light attenuating tissues as much as possible. When lead 16 is positioned extra-thoracically, emitting device 18 may be positioned inferior to the xyphoid process 20 in a position approximately as shown. In other examples, emitting device 18 is positioned relative to pacemaker 100 to establish an efficient optical transmission pathway that takes into account the optical properties of the surrounding and intervening tissues.

Defibrillation lead 16 may include an attachment feature 29 at or toward the distal end of lead 16. The attachment feature 29 may be a loop, link, suture or other attachment feature useful to aid in implantation of lead 16 and/or for securing lead 16 to a desired implant location. In some instances, defibrillation lead 16 may include a fixation mechanism in addition to or instead of the attachment feature 29. For example, defibrillation lead 16 may include a suture sleeve or other fixation mechanism (not shown) located proximal to electrode 30 or near emitting device 18 that is configured to fixate lead 16 near the xiphoid process 20 or lower sternum location. The fixation mechanism (e.g., suture sleeve or other mechanism) may be integral to the lead or may be added by the user prior to implantation. The fixation mechanism may be used to stably locate emitting device 18 inferior to the xyphoid process 20, along an intercostal space, or other desired location to prevent rotation or shifting of the emitting device 18 that may cause trigger signal misdirection or trigger signal loss due to interference or attenuation by body tissues.

Although ICD 14 is illustrated as being implanted near a midaxillary line of patient 12, ICD 14 may also be implanted at other subcutaneous locations on patient 12, such as further posterior on the torso toward the posterior axillary line, further anterior on the torso toward the anterior axillary line, in a pectoral region, or at other locations of patient 12. In instances in which ICD 14 is implanted pectorally, lead 16 would follow a different path, e.g., across the upper chest area and inferior along sternum 22. When the ICD 14 is implanted in the pectoral region, the system 10 may include a second lead including a defibrillation electrode, and optionally an optical emitting device, that extends along the left side of the patient such that the defibrillation electrode of the second lead is located along the left side of the patient to function as an anode or cathode of the therapy vector for defibrillating heart 26.

ICD 14 includes a housing 15 that forms a hermetic seal that protects components within ICD 14. Housing 15 may enclose one or more components, including processors, memories, transmitters, receivers, sensors, sensing circuitry, therapy circuitry and other appropriate components (often referred to herein as modules). The housing 15 of ICD 14 may be formed of a conductive material, such as titanium or other biocompatible conductive material or a combination of conductive and non-conductive materials. In some instances, the housing 15 functions as an electrode (sometimes referred to as a housing electrode or can electrode) that is used in combination with one of electrodes 24, 28 and 30 to deliver a therapy to heart 26 or to sense electrical activity of heart 26.

ICD 14 may include a connector assembly 13 (sometimes referred to as a connector block or header) for receiving a proximal connector (not illustrated) of lead 16. Connector assembly 13 includes electrical feedthroughs through which electrical connections are made between conductors within defibrillation lead 16 and electronic components included within the housing 15. Depending on the intended implant location of ICD 14, an optical emitting device 18 may be included in connector assembly 13 and/or housing 15 in addition to or in place of the emitting device 18 carried by lead 16 for transmitting optical trigger signals to pacemaker 100. For example, an optical emitting device may be embedded, e.g. overmolded, in the connector assembly or included in a wafer-scale hermetic package incorporated in connector assembly 13 and coupled to feedthroughs extending into housing 15 for receiving control signals from ICD internal circuitry.

Lead 16 may include a connector at the proximal end of lead 16, such as a DF4 connector, bifurcated connector (e.g., DF-1/IS-1 connector), or other type of connector having at least one terminal pin that couples to a port within the connector assembly 13 of ICD 14. The lead body 17 of defibrillation lead 16 may be formed from a non-conductive material, including silicone, polyurethane, fluoropolymers, mixtures thereof, and other appropriate materials, and shaped to form one or more lumens within which the one or more elongated conductors extend.

Defibrillation lead 16 includes elongated electrical conductors (not illustrated) that each extend within the elongated lead body 17 from the connector on the proximal end of defibrillation lead 16 to respective electrodes 24, 28 and 30 and emitting device 18. Although defibrillation lead 16 is illustrated as including three electrodes 24, 28 and 30, defibrillation lead 16 may include more or fewer electrodes. When the connector of defibrillation lead 16 is connected to connector assembly 13, the respective conductors may electrically couple to circuitry, such as a therapy delivery module or a sensing module, or a trigger signal drive signal circuit of ICD 14 via connections in connector assembly 13, including associated feedthroughs.

The electrical conductors transmit electrical stimulation pulses from a therapy module within ICD 14 to one or more of electrodes 24, 28 and 30 and transmit sensed electrical signals from one or more of electrodes 24, 28 and 30 to the sensing module within ICD 14. An electrical conductor extending from the proximal lead connector to emitting device 18 conducts a control signal to emitting device 18 to cause emitting device 18 to emit an optical trigger signal at appropriate times for causing intracardiac pacemaker 100 to deliver one or more pacing pulses to heart 26.

ICD 14 may sense electrical activity of heart 26 via one or more sensing vectors that include combinations of electrodes 28 and 30 and housing 15. For example, ICD 14 may obtain cardiac electrical signals using a sensing vector between electrodes 28 and 30, between electrode 28 and the conductive housing 15, between electrode 30 and housing 15, or any combination thereof. In some instances, ICD 14 may even sense cardiac electrical signals using a sensing vector that includes defibrillation electrode 24, such as a sensing vector between defibrillation electrode 24 and one of electrodes 28 and 30, or a sensing vector between defibrillation electrode 24 and the housing 15.

ICD 14 determines a need for pacing therapy in response to the sensed cardiac electrical signals, which may include P-waves and R-waves for example, and controls emitting device 18 to emit optical trigger signals based on that determination. The need for pacing pulses may be determined according to programmed single chamber, dual chamber or multi-chamber bradycardia or CRT control parameters other cardiac pacing therapy parameters. ICD 14 may also analyze the sensed electrical signals to detect tachycardia, such as ventricular tachycardia or ventricular fibrillation, and in response to detecting tachycardia may generate and deliver an electrical therapy to heart 26. For example, ICD 14 may deliver one or more defibrillation shocks via a therapy vector that includes defibrillation electrode 24 and the housing 15.

Electrodes 24, 28, 30 and housing 15 may be used for sensing ECG signals for use in controlling the timing of an R-wave synchronized shock delivered by ICD 14 and for controlling timing of pacing pulses delivered by pacemaker 100. In some instances, one or more pacing therapies may be delivered prior to or after delivery of a defibrillation shock by ICD 14, such as anti-tachycardia pacing (ATP) or post shock pacing. In these instances, ICD 14 may generate and deliver pacing pulses via therapy vectors that include electrodes 24, 28, 30 and/or housing 15. Alternatively, ICD 14 may cause optical emitting device 18 to emit trigger signals to cause pacemaker 100 to deliver pacing pulses to heart 26 at appropriate times when ATP or post-shock pacing is needed as well as for bradycardia or CRT pacing therapies is needed.

The example ICD 14 illustrated in FIG. 2A is illustrative in nature and should not be considered limiting of the sensing device used in a triggered therapy delivery system and associated techniques described in this disclosure. For instance, in addition to sensing ECG signals, ICD 14 may include shock therapy capabilities only without pacing therapy capabilities. In other examples, ICD 14 may be coupled to more than one lead for sensing ECG signals and/or sending trigger signals to pacemaker 100. In still other examples, a sensing device may be substituted for ICD 14 that is a single chamber or dual chamber subcutaneous pacemaker without cardioversion/defibrillation capabilities or a sensing-only device without therapy delivery capabilities, e.g., as shown in FIG. 1B. Any of these sensing devices may be coupled to housing-based electrodes and/or electrodes carried by a transvenous, intracardiac or extravascular, extracardiac lead for sensing a cardiac electrical signal and determining appropriate times for triggering pacemaker 100 to delivery therapy.

Pacemaker 100 is a transcatheter, intracardiac pacemaker adapted for implantation wholly within a heart chamber, e.g. wholly within the RV, wholly within the LV, wholly within the right atrium (RA) or wholly within the left atrium (LA) of heart 26. In the example of FIG. 2, pacemaker 100 is positioned proximate to an inner wall of the LV to provide left ventricular pacing. In other examples, pacemaker 100 is positioned proximate to an inner wall of the right ventricle to provide right ventricular pacing. In other examples, pacemaker 100 may be positioned at any other location outside or within heart 26. For example, IMD 16 may be positioned outside or within the right atrium or left atrium, e.g., to provide respective right atrial and left atrial pacing. In other embodiments, pacemaker 100 may be embodied as a therapy delivery device for delivering an electrical stimulation therapy at another body location. Pacemaker 100 is shown as a leadless device in FIG. 2. It is contemplated, however that in other embodiments pacemaker 100 may be coupled to a lead extending from pacemaker 100 to position therapy delivery electrodes at a location spaced apart from pacemaker 100.

Depending on the implant location, pacemaker 100 may be configured to deliver an electrical stimulation therapy to therapy delivery site(s) other than the myocardium. For example, pacemaker 100 may provide atrioventricular nodal stimulation, fat pad stimulation, vagal stimulation, or other types of neurostimulation. In other examples, system 10 may include a plurality of pacemakers 100, e.g., to deliver electrical stimulation therapy at multiple sites, such as within multiple heart chambers for multi-chamber pacing therapies.

Pacemaker 100 is capable of producing electrical pacing pulses delivered to heart 26 via one or more electrodes on the outer housing of pacemaker 100. Pacemaker 100 includes a light detector for receiving an optical trigger signal emitted by emitting device 18. In response to detecting an optical trigger signal, pacemaker 100 delivers one or more pacing pulses.

In one embodiment, pacemaker 100 includes a pulse generator configured to deliver one or more pacing pulses upon receiving an optical trigger signal from emitting device 18. Pacemaker 100 may not be configured to sense cardiac signals. Cardiac signal sensing is performed by ICD 14. ICD 14 senses ECG signals through lead 16 and controls pacing delivered by pacemaker 100 via optical trigger signals emitted by emitting device 18 under the control of ICD 14.

Intracardiac pacemaker 100 may not be configured to sense cardiac signal signals. Pacemaker 100 may rely solely on a trigger signal from emitting device 18 for controlling the timing of pacing pulse delivery without sensing any other cardiac electrical event signals or any other physiological signals. As a result, the ability to independently deliver CRT or other types of pacing therapies that are synchronized with paced or sensed events occurring in another cardiac chamber may be limited. In order to minimize the size of pacemaker 100, cardiac signal sensing and radio frequency telemetry functions may be omitted such that pacemaker 100 includes a pulse generator with limited memory, processing, and other functions directed to therapy delivery.

In other embodiments, pacemaker 100 senses EGM signals in the heart chamber in which it is implanted. Since pacemaker 100 is positioned wholly within a heart chamber, the EGM signal sensed by pacemaker 100 will be less sensitive or insensitive to P-waves and/or R-waves occurring in other heart chambers. In past practice, a subcutaneous pacemaker might be coupled to one or more leads that position sense electrodes in or along multiple heart chambers such that multiple sensing channels can be monitored. By monitoring multiple sensing channels, coordinated pacing pulses can be delivered to one or more heart chambers at specified time intervals, e.g., AV or W intervals.

Since pacemaker 100 may have no or limited sensing capabilities, pacemaker 100 may be "blinded" to events occurring in other heart chambers. Delivery of CRT, dual chamber pacing, or other multi-chamber pacing therapies may require delivering a pacing pulse at a predetermined time interval after an event, sensed or paced, in another heart chamber. As such, emitting device 18 provides a trigger signal to pacemaker 100 in response to ECG signals sensed by ICD 14 to cause pacing pulses to be delivered by pacemaker 100 at desired time intervals relative to other heart chamber events. Pacemaker 100 (for generating pacing pulses) combined with ICD 14 (for sensing physiological signals for making therapy delivery decisions) provides the functionality required to deliver various therapies that may require synchronization or coordination between multiple anatomical sites without physical connection between pacemaker 100 and ICD 14 implanted at separate sites.

FIG. 2A further depicts programmer 40 in wireless communication with ICD 14 via communication link 42. In some examples, programmer 40 comprises a handheld computing device, computer workstation, or networked computing device. Programmer 40 includes a user interface that presents information to and receives input from a user. It should be noted that the user may also interact with programmer 40 remotely via a networked computing device.

A user, such as a physician, technician, surgeon, electrophysiologist, other caregiver, or patient, interacts with programmer 40 to communicate with ICD 14. For example, the user may interact with programmer 40 to retrieve physiological or diagnostic information from ICD 14. A user may also interact with programmer 40 to program ICD 14, e.g., select values for operational parameters of the ICD 14, including parameters used to control optical trigger signal emitting device 18 for controlling pacemaker 100. A user may use programmer 40 to retrieve information from ICD 14 regarding the rhythm of heart 26, trends therein over time, or arrhythmic episodes.

As indicated, ICD 14 and programmer 40 communicate via wireless communication. Examples of communication techniques include, for example, low frequency or radiofrequency (RF) telemetry, but other techniques may be used. In some examples, programmer 40 may include a programming head that is placed proximate to the patient's body near the ICD 14 implant site in order to improve the quality or security of communication between ICD 14 and programmer 40.

Figure 2B:
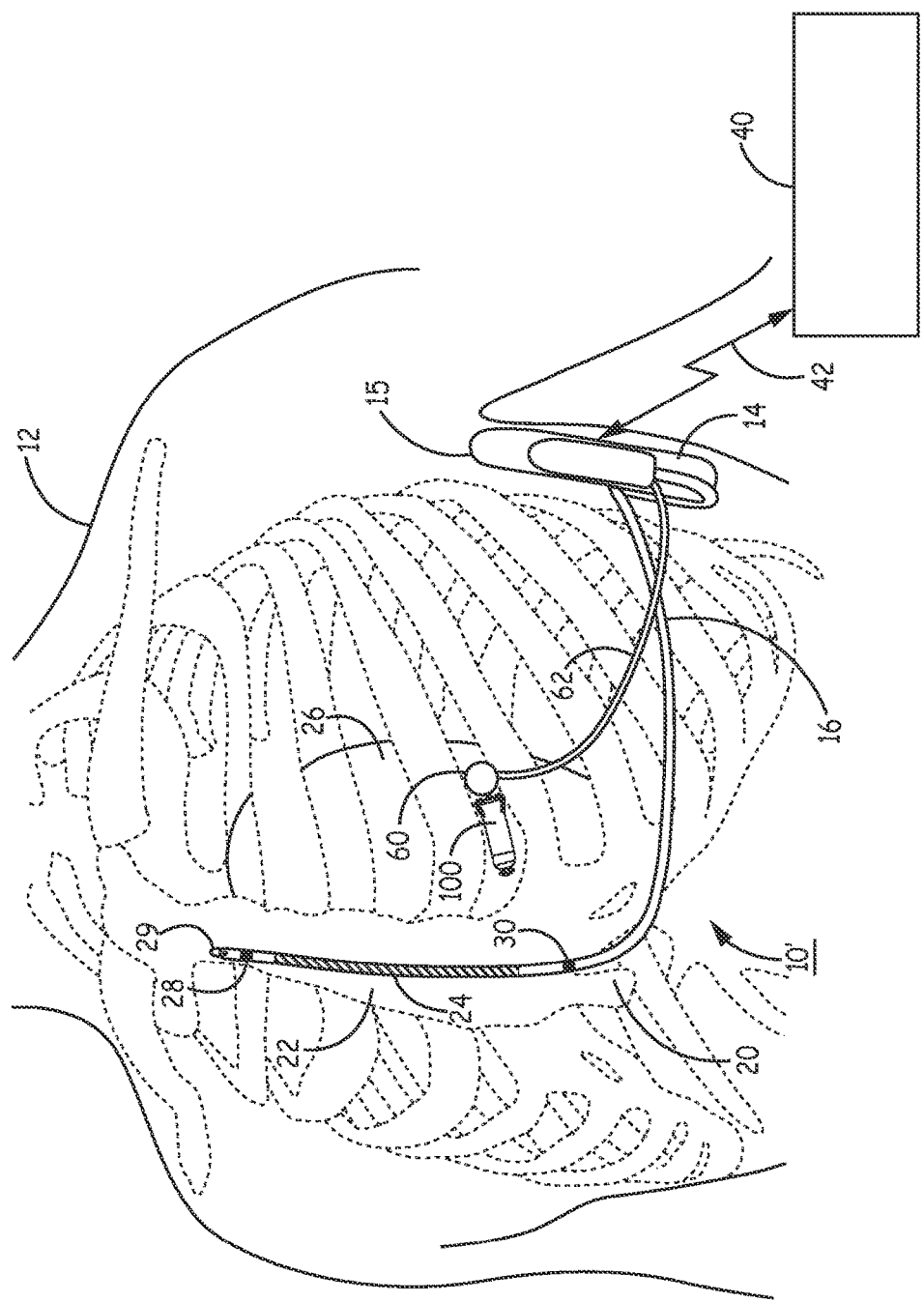
FIG. 2B is a conceptual diagram illustrating an IMD system 10' according to an alternative example.

FIG. 2B is a conceptual diagram illustrating an IMD system 10' according to an alternative example. A dedicated lead 62 carrying an optical signal emitting device 18 may be provided to position emitting device 18 at an optimal location for transmitting an optical trigger signal to pacemaker 100. An optimal location would position emitting device 60 relative to pacemaker 100 such that an optical trigger signal reaches pacemaker 100 with adequate intensity and signal-to-noise ratio to be reliably sensed by pacemaker 100. An optical path between emitting device 60 and pacemaker 100 may include tissues that scatter, absorb, reflect or refract the optical trigger signal. The location of emitting device 60 is selected such that the optical signal losses along the path do not reduce the intensity of the trigger signal below a threshold level that is detectable by pacemaker 100.

Emitting device 60 is capable of receiving a control signal from ICD 14 conducted along lead 62. Upon receipt of the control signal, emitting device 60 emits an optical trigger signal to cause pacemaker 100 to deliver an LV pacing pulse. Emitting device 60 may have its own battery, which may be rechargeable, such that the power required by ICD 14 for sensing and therapy delivery functions and the power required for optical trigger signal emission is distributed across two devices and two (or more) batteries or other power sources.

Figure 3A:
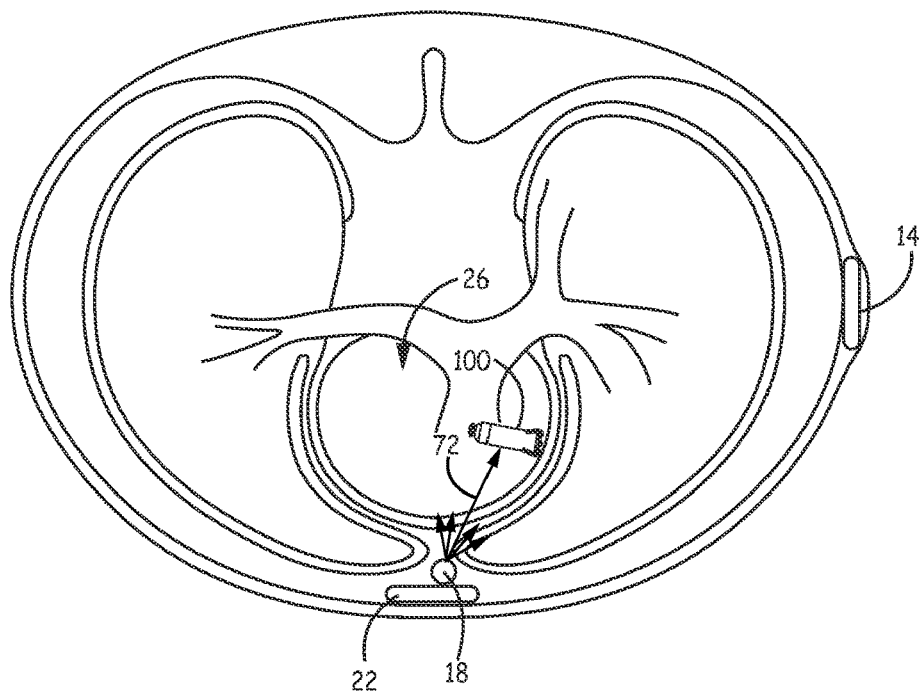
FIGS. 3A and 3B are sectional views of the patient's anatomy depicting alternative configurations of an optical trigger signal emitting device included in the system shown in FIG. 2A.
Figure 3B:
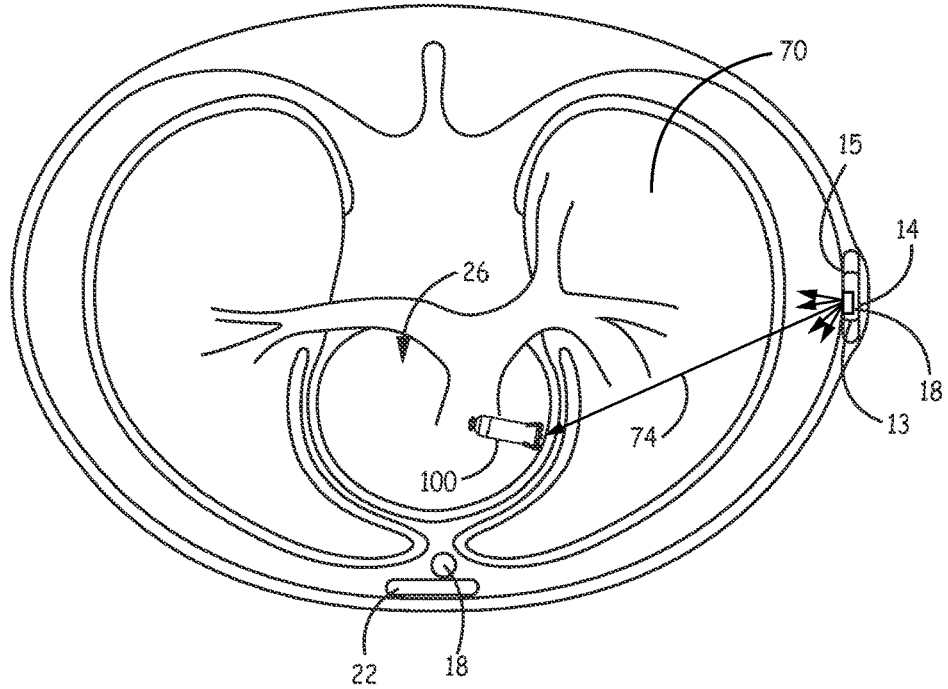

FIGS. 3A and 3B are sectional views of the patient's anatomy depicting alternative configurations of an emitting device in system 10. Emitting device 18 is shown in a substernal position on lead 16 (not seen in the sectional view of FIG. 3A). Instead of being positioned suprasternally, inferior to the xyphoid process, emitting device 18 may be positioned substernally and relatively more superior by advancing the distal end of lead 16 to a substernal location. As shown, emitting device 18 is configured for hemispherical light emission generally directed toward an implant position of pacemaker 100 within heart 26 and encompassing an optical path to pacemaker 100 as represented by arrow 72. An optical path 72 from emitting device 18 to pacemaker 100 extends through the myocardium to pacemaker 100 without traversing the sternum 22. Pacemaker 100 delivers therapeutic stimulation pulses to heart 26 under the control of ICD 14 via optical trigger signals emitted by emitting device 18.

Lead 16 may be placed under or below the sternum in the mediastinum and, more particularly, in the anterior mediastinum. The anterior mediastinum is bounded laterally by pleurae, posteriorly by pericardium, and anteriorly by sternum. Lead 16 may be at least partially implanted in other extra-pericardial locations, i.e., locations in the region around, but not necessarily in direct contact with, the outer surface of heart 26. These other extra-pericardial locations may include in the mediastinum but offset from sternum 22, in the superior mediastinum, in the middle mediastinum, in the posterior mediastinum, in the sub-xiphoid or inferior xiphoid area, near the apex of the heart, or other location not in direct contact with heart 26 and not subcutaneous. In other embodiments, lead 16 may extend within the pericardium and in direct contact with heart 26. In any of these illustrative implant locations, lead 16 may be positioned to optimally position optical emitting device 18 for reliably transmitting a trigger signal to pacemaker 100.

In FIG. 3B, ICD 14 is shown configured to include light emission capabilities. In some embodiments, an emitting device 18 may be included in ICD 14 in addition to or alternatively to a lead-based emitting device. ICD 14 may include an emitting device 18 in a lead connector block 13 or exposed along the ICD housing 15 through an optically conductive light window in the housing 15. ICD 14 is coupled to lead 16, which may extend suprasternally or substernally, for sensing ECG signals using electrodes carried by lead 16 as described above.

An emitting device 18 positioned external to the ribcage, such as in or along ICD 14 or positioned subcutaneously along a lead extending from ICD 14, may be positioned such that light is directed toward pacemaker 100 in heart 26 through an intercostal space and lung tissue, such as left lung 70. Transmission of an optical trigger signal along an optical path represented by arrow 74 through lung tissue may be more efficient than an optical path 72 (FIG. 3A) that may extend through a blood volume. As described below, the wavelength of an optical trigger signal is selected to provide efficient transmission through or off of the tissues, e.g. muscle, blood, bone, lung, etc., along an optical path between the optical trigger signal emitting 18 device and the receiving pacemaker 100.

Figure 4A:
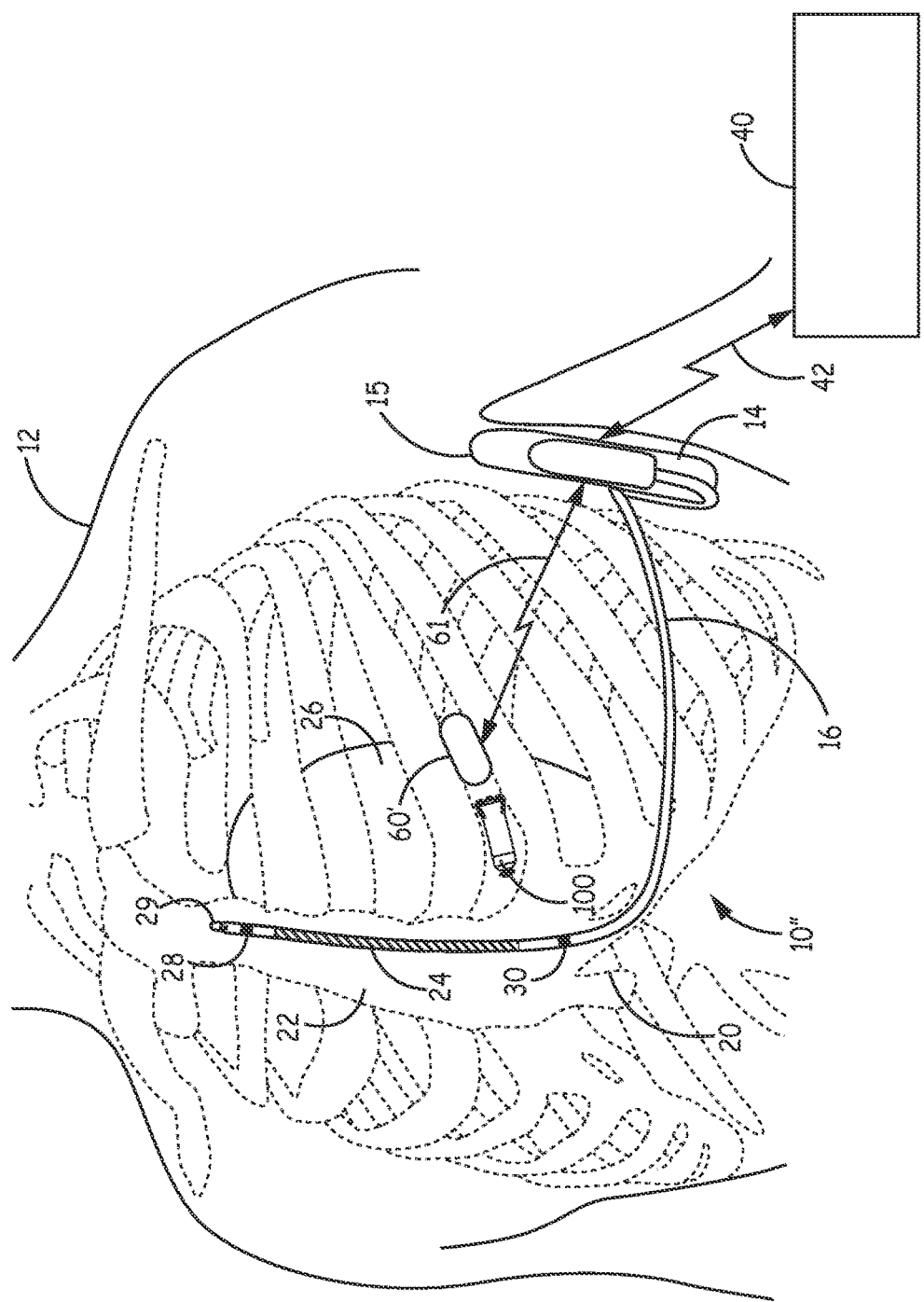
FIG. 4A is a conceptual diagram illustrating an IMD system according to an alternative example.

FIG. 4A is a conceptual diagram illustrating an implantable medical device (IMD) system 10" according to an alternative example. ICD 14 coupled to lead 16 is used to sense cardiac electrical signals in patient 12 and provide therapy to heart 26 as described above. Intracardiac pacemaker 100 is implanted within the LV and delivers pacing pulses to the LV in response to receiving an optical trigger signal. In this embodiment, a leadless optical trigger signal emitting device 60' is positioned extrathoracically, along an intercostal space, to direct an optical trigger signal toward pacemaker 100 through the intercostal space and intervening muscle and lung tissue.

Emitting device 60' is capable of receiving a wireless control signal 61 from ICD 14. Upon receipt of control signal 61, leadless emitting device 60' emits an optical trigger signal to cause pacemaker 100 to deliver an LV pacing pulse. Emitting device 60' may have its own battery, which may be rechargeable.

Leadless emitting device 60' may be positioned at an optimal location for transmitting an optical trigger signal to pacemaker 100 without limitations associated with optimal positioning of electrodes 24, 28 and 30 for sensing ECG signals and delivering shock therapy. Leadless emitting device 60 may be implanted at a desired site without requiring lead tunneling. The leadless emitting device 60 may act as a relay device for transmitting a control signal 61 from ICD 14 to pacemaker 100 by converting the wirelessly transmitted control signal 61 to an optical trigger signal. ICD 14, for example, may transmit an RF control signal 61 that is received by an RF receiver included in leadless emitting device 60. Leadless emitting device 60 converts the RF signal to an optical signal that is transmitted as an optical trigger signal to pacemaker 100.

The control signal 61 originating from ICD 14 may be an optical signal in some examples. Since more electrically efficient signals may be used for triggering the emitting device 60 to emit an optical signal, however, the control signal may a telemetric communication signal that is not an optical signal. It is contemplated, however, that the ICD 14 may pass an optical control signal 61 to emitting device 60 that acts as an optical relay device. The emitting device 60 may alternate between send and receive modes where it receives an optical control signal from ICD 14 then transmits the optical trigger signal on to the pacemaker 100.

In some examples, multiple emitting devices may be included in systems 10, 10' or 10". Depending on the final implant position of pacemaker 100 and shifting that may occur over time, pacemaker 100 may be more sensitive to an optical trigger signal emitted by one device at one location than by another device at a different location. Multiple emitting devices positioned at different, spaced apart locations may be selected individually or in combination by ICD 14 to emit an optical trigger signal to achieve reliable trigger signal detection by pacemaker 100 using the greatest power efficiency.

Figure 4B:
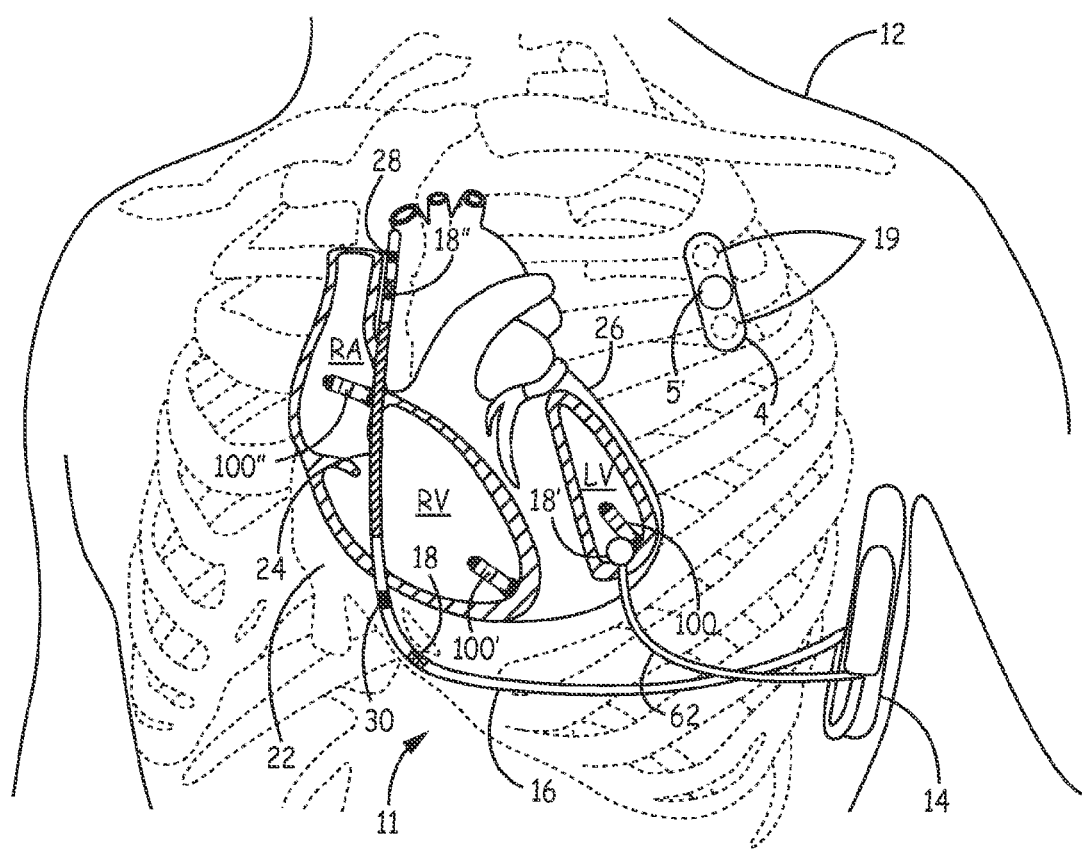
FIG. 4B is a conceptual diagram illustrating an IMD system including multiple therapy delivery devices.

FIG. 4B is a conceptual diagram illustrating an IMD system 11 including multiple therapy delivery devices 100, 100', and 100". In embodiments including multiple intracardiac pacemakers 100, 100' and 100" the light detectors in each pacemaker 100, 100', and 100" may be configured to be sensitive to different wavelengths. In the example shown, one pacemaker 100 is shown in the LV, pacemaker 100' is shown in the RV and pacemaker 100" is shown in the RA. Emitting device 18 may be controlled to emit light at a first wavelength for triggering an RV pacemaker 100' sensitive to the first wavelength and to emit a second wavelength for triggering an LV pacemaker 100 sensitive to the second wavelength. The emitting device 18 may be controlled by ICD 14 to emit a trigger signal at the first wavelength to cause delivery of an optically-triggered RV pacing pulse and emit a trigger signal at the second wavelength to trigger an LV pacing pulse at a controlled time interval (positive or negative) relative to the triggered pace in the RV. Similarly, RA pacemaker 100" may be triggered to deliver a pacing pulse in response to a third wavelength.

As described below, each of pacemakers 100, 100' and 100" may include a programmable wavelength light detector in which one of multiple selectable photosensitive components, including one or more photodetectors, one or more photodiodes, one or more photoresistors, etc., is selected for receiving a particular trigger signal wavelength.

Alternatively, multiple triggered pacemakers 100, 100' and 100" may include light detectors for detecting trigger signals at the same wavelength but configured to detect different trigger signal patterns that are mutually exclusive. For example, a given triggered pacemaker 100, 100' or 100" may be configured to detect a trigger signal including multiple light pulses at defined pulse intervals, pulse amplitudes and/or other pulse shaping parameters or patterns. An individual triggered pacemaker 100 may be addressed by a specified trigger signal pattern while another triggered pacemaker 100' or 100" is addressed by a different trigger signal pattern. Different trigger signal parameters may be used to transmit mutually exclusive trigger signals that are recognized and detected by the appropriate therapy delivery device 100, 100' or 100". Mutually exclusive trigger signal patterns may be defined by different optical signal pulse numbers, different interpulse intervals, different pulse widths, different rising and/or falling slope of a trigger signal pulse or any combination thereof.

To illustrate, one therapy delivery device 100 may detect a trigger signal having more than two pulses as invalid while another therapy delivery 100' or 100" device may require detection of a minimum of three pulses to recognize a valid trigger signal. In another example, one therapy delivery device 100 may detect a valid trigger signal having a short-long-short interpulse interval pattern and another therapy delivery device 100' or 100" may detect a valid trigger signal as one having a long-short-long interpulse interval pattern.

Alternatively, when two or more therapy delivery devices 100, 100' and 100" are included in the IMD system 11, multiple emitting devices 18, 18' and 18", each configured to target a trigger signal at one specific therapy device, 100', 100 and 100", respectively, may be used. For example, paired emitting and therapy delivery devices, e.g., 18 paired with 100', 18' paired with 100, and 18" paired with 100", may be implanted relative to each other within an optical trigger signal range so that each emitting device 18, 18' and 18" is positioned and controlled to deliver the emitted optical trigger signal at a respective therapy delivery device 100', 100, and 100", respectively.

Each of emitting devices 18, 18" and 18''' are shown carried by leads 16 and 62 coupled to ICD 14 but in some examples an emitting device 5' included in an IMD system 11 may be controlled by a sensing-only device 4, which may be provided as an ECG monitor as described in conjunction with FIG. 1A. Emitting device 5' may be one of multiple emitting devices used to control multiple therapy delivery devices 100, 100' and 100" or a single emitting device of IMD system 11 used to control the multiple therapy delivery devices 100, 100' and 100".

The multiple therapy delivery devices 100, 100' and 100", emitting devices 18, 18' and 18" and sensing devices 4 and 14 shown in FIG. 3B are depicted to illustrate various possible combinations of one or more sensing device, one or more emitting device and/or one or more therapy delivery device that could be included in an IMD system 11 that controls at least one triggered therapy delivery device using an optical trigger signal. Any variation or combination of these devices may be used to deliver a therapy triggered by an optical trigger signal. A therapy delivery system employing the techniques disclosed herein may include different combinations and arrangements of at least one therapy delivery device, at least one sensing device and at least one trigger signal emitting device than the combinations and arrangements shown in the accompanying drawings.

Figure 5:
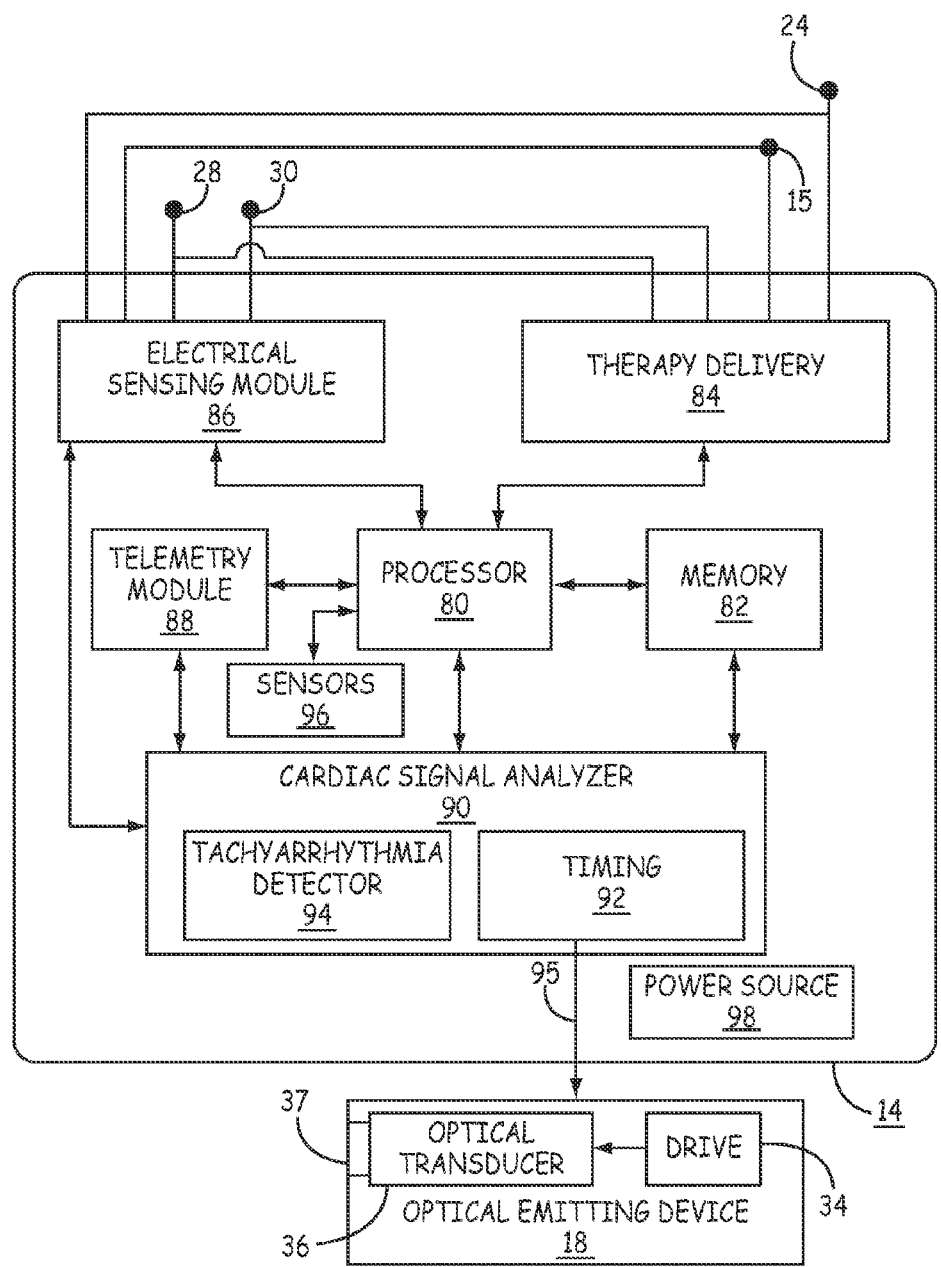
FIG. 5 is a functional block diagram of electronic circuitry that is included in one embodiment of the implantable cardioverter defibrillator (ICD) shown in FIG. 2.

FIG. 5 is a functional block diagram of electronic circuitry that is included in one embodiment of ICD 14. The ICD 14 includes processing and control module 80, also referred to herein as "control module" 80, memory 82, therapy delivery module 84, electrical sensing module 86, telemetry module 88 and cardiac signal analyzer 90. A power source 98 provides power to the circuitry of ICD 14, including each of the modules 80, 82, 84, 86, 88, and 90. Power source 98 may include one or more energy storage devices, such as one or more chargeable or non-re-chargeable batteries.

The functional blocks shown in FIG. 5 represent functionality that may be included in ICD 14 and may include any discrete and/or integrated electronic circuit components that implement analog and/or digital circuits capable of producing the functions attributed to ICD 14 herein. For example, the modules may include analog circuits, e.g., amplification circuits, filtering circuits, and/or other signal conditioning circuits. The modules may also include digital circuits, e.g., analog-to-digital converters, combinational or sequential logic circuits, integrated circuits, memory devices, etc. Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control module 80 or other ICD modules to perform various functions attributed to ICD 14. The non-transitory computer readable media storing the instructions may include any of the media listed above, with the sole exception being a transitory propagating signal. The particular form of software, hardware and/or firmware employed to implement the functionality disclosed herein will be determined primarily by the particular system architecture employed in the IMD system devices. Providing software, hardware, and/or firmware to accomplish the described functionality in the context of any modern IMD system, given the disclosure herein, is within the abilities of one of skill in the art.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common hardware or software components. For example, cardiac signal monitoring may be performed by cardiac signal analyzer 90 for determining a need for therapy delivered by ICD 14 and/or pacemaker 100 or implemented in control module 80 executing instructions stored in memory 82.

Processing and control module 80 communicates with therapy delivery module 84, cardiac signal analyzer 90 and electrical sensing module 86 for sensing cardiac electrical activity, detecting cardiac rhythms, and generating cardiac therapies in response to sensed signals. Therapy delivery module 84 and electrical sensing module 86 are electrically coupled to electrodes 24, 28, and 30 carried by lead 16 as shown in FIG. 2A and housing 15, at least a portion of which also serves as a common or ground electrode.

Electrical sensing module 86 is coupled to electrodes 28 and 30 in order to monitor electrical activity of the patient's heart. Electrical sensing module 86 may optionally be coupled to electrodes 24 and 15 and enabled to selectively monitor one or more sensing vector selected from the available electrodes 24, 28, 30 and 15. For example, sensing module 86 may include switching circuitry for selecting which of electrodes 24, 28, 30 and housing electrode 15 are coupled to sense amplifiers included in sensing module 86. Switching circuitry may include a switch array, switch matrix, multiplexer, or any other type of switching device suitable to selectively couple sense amplifiers to selected electrodes. A sensing vector between electrodes 28 and 30 may be selected for sensing an ECG signal or sensing vector may be selected that utilizes coil electrode 24 and/or housing 15, e.g., from sensing electrode 28 to housing 15 or from sensing electrode 30 to housing 15.

One or more ECG signals are passed to the input of sensing module 86, which includes one or more sense amplifiers or other cardiac event detection circuitry for sensing cardiac events, e.g., P-wave and/or R-waves, from the ECG signal(s). Sensing module 86 includes sense amplifiers that pass sense event signals to cardiac signal analyzer 90. For example P-wave sense signals and R-wave sense signals are passed to cardiac signal analyzer 90 when the ECG signal crosses a respective P-wave sensing threshold and R-wave sensing threshold, which may each be auto-adjusting sensing thresholds. Bradycardia or asystole is typically determined by a pacing escape interval timer expiring within the timing circuit 92. In response to the pacing escape interval expiring, a control signal 95 is passed to the optical emitting device 18. The pacing escape interval is restarted upon a pacing pulse trigger or a sense event signal. Other pacing intervals, such AV or VV pacing intervals are started by control module 80 upon sensing an event in one cardiac chamber, atrial or ventricular, and sending a trigger signal to pacemaker 100 to deliver a pacing pulse synchronized to the sensed event at the AV or VV interval.

The control signal 95 in the illustrative examples presented herein may be referred to as a pacing control signal because it causes pacemaker 100 to deliver a pacing pulse to a heart chamber. In other examples, the control signal 95 may be produced by cardiac signal analyzer 90 to cause other types of therapy pulses to be delivered by a therapy delivery device such as pacemaker 100. For example control signal 95 may be produced to cause pacemaker 100 or another therapy delivery device to deliver an ATP pulse, a vagal nerve stimulation pulse, or other type of electrical stimulation pulse.

The control signal 95 is an electrical signal that is passed to emitting device 18 along lead 16 (or another lead carrying emitting device 18) when emitting device is coupled to ICD 14 in a wired connection. The control signal 95 is alternatively an electrical signal that is passed to telemetry module 88 where it is converted to a wireless telemetry signal that is transmitted via telemetry module 88, to emitting device 18. Emitting device 18 may be carried by a lead but configured to wirelessly receive a control signal 95 from telemetry module 88. Alternatively, the emitting device is not a lead-based emitting device, such as leadless emitting device 60' shown in FIG. 4A, and receives wireless control signals, e.g. RF signals, from telemetry module 88.

Optical emitting device 18 includes a drive signal circuit 34 that receives the control signal 95, either as a wired electrical signal or a wireless signal from telemetry module 88. It is understood that in some embodiments, drive signal circuit 34 may be included within the housing 15 of ICD 14 and coupled to transducer 36 located external to housing 15.

Drive signal circuit 34 passes an electrical signal to optical transducer 36 to enable optical transducer 36 to emit an optical trigger signal. As described herein, the optical trigger signal is received and detected by pacemaker 100 to cause pacemaker 100 to deliver one or more pacing pulses to the patient's heart. The optical trigger signal may be generated according to pre-set intensity, wavelength, and signal duration and other signal characteristics. In other words, the control signal may only signal the emitting device 18 that a trigger signal is needed. The trigger signal merely signals pacemaker 100 to delivery therapy without signaling any information relating to how many pacing pulses, what pulse amplitude or pulse width or other pacing pulse control parameter information. Pacemaker 100 may be programmed to deliver a predetermined number of pacing pulses according to predefined pulse control parameters when the trigger signal is detected.

Alternatively, control signal 95 may include encoded pacing pulse control information. The control signal generated by drive signal circuit 34 may cause transducer 36 to emit a trigger signal according to an intensity, wavelength, signal duration and/or other characteristic of the optical trigger signal that is intentionally adjusted according to the control signal. In this case, the control signal 95 signals the emitting device 18 that a trigger signal is needed as well as what characteristic(s) the emitted trigger signal should have. Pacemaker 100 may be configured to detect the characteristic(s) of the emitted trigger signal and set a pacing pulse control parameter based on that characteristic.

Optical transducer 36 may include multiple light emitting transducers. Optical transducer 36 may include multiple transducers configured to emit optical signals in multiple directions from emitting device 18 to promote reception of the optical trigger signal by pacemaker 100 despite shifting, rotation or other changes of the relative orientations of emitting device 18 and pacemaker 100 with respect to each other. The multiple transducers may be selectable by drive circuit 34 such that a transducer producing the best signal-to-noise ratio at the pacemaker light detector is selected. Optical transducer 36 may include multiple different transducers or light emitting devices that are selectable by drive circuit 34 to enable transmission of different trigger signals, e.g., different trigger signal wavelengths, for triggering different intracardiac pacemakers as described in conjunction with FIG. 4B, and/or triggering different types of pacing pulses or therapies (e.g. different pulse shape, pulse amplitude, pulse width, pulse frequency, etc).

Optical transducer 36 includes one or more collimated or non-collimated light sources, such as one or more light emitting diode (LED), one or more vertical cavity surface emitting laser (VCSEL), Quantum Dot Light Emitting Device (QD-LED), Quantum Dot Laser, organic LED, discharge/strobe light, or other light source having a high quantum efficiency at a selected light wavelength. Optical transducer 36 includes any opto-electronic device having a photonic surface directed toward a window 37 that may include a transparent lens and an optical coupling medium or member for increasing the efficiency of light emitted from the emitting device 18. Optical transducer 36 may be configured to emit light through a window 37 according to examples generally disclosed in commonly-assigned U.S. Pat. No. 8,275,432 (Kuhn, et al.) and U.S. Pat. No. 8,452,402 (Ecker, et al.), both of which patents are hereby incorporated herein by reference in its entirety.

The optical transducer 36 has an emitted light bandwidth that is selected to provide a transmission intensity that is detectable by the pacemaker light detector after attenuation due to tissue absorption and light scattering losses along the optical pathway between the optical transducer 36 and the pacemaker light detector. Generally, as wavelength increases scattering decreases monotonically. Absorption increases with increasing wavelength, but local minima occur in the absorption spectra. Accordingly, a trigger signal wavelength may be selected that takes into account the effects of both absorption and scattering on the resulting signal intensity at the pacemaker light detector.

For example, a light emitting device having a signal bandwidth with a center frequency at a local minima on the absorption spectra may be selected. As wavelength increases, the absorption spectrum transitions from being hemoglobin-dependent to being water-dependent. As such, a relatively high center wavelength, e.g. greater than approximately 1000 nm, may be selected. Wavelengths of approximately 1,100 nm, 1,300 nm, and 1,700 nm are each associated with a local minimum of the absorption spectrum for water. Any of these examples, without limitation, may be selected as a center wavelength of the optical trigger signal bandwidth. An optical pathway between the emitting device and the pacemaker may extend through multiple tissues having varying optical properties. Accordingly, a number of considerations may be taken into account when selecting the type and center wavelength of the optical transducer 36 and its implant location.

Timing circuit 92 may generate a control signal 95 to trigger pacemaker 100 to deliver pacing pulses to provide bradycardia pacing, atrial-synchronized ventricular pacing, ATP, CRT, AV nodal stimulation, or other pacing therapies according to pacing algorithms and timing intervals stored in memory 82. Bradycardia pacing may be delivered temporarily to maintain cardiac output after delivery of a cardioversion-defibrillation shock by ICD 14 as the heart recovers back to normal function post-shock.

Cardiac signal analyzer 120 includes a tachyarrhythmia detector 94 for detecting and discriminating supraventricular tachycardia (SVT), ventricular tachycardia (VT) and ventricular fibrillation (VF). Some aspects of sensing and processing subcutaneous ECG signals are generally disclosed in commonly-assigned U.S. Pat. No. 7,904,153 (Greenhut, et al.), hereby incorporated herein by reference in its entirety. The timing of R-wave sense signals from sensing module 86 is used by tachyarrhythmia detector 94 to measure R-R intervals for counting RR intervals in different detection zones or determining a heart rate or other rate-based measurements for detecting ventricular tachyarrhythmia. Electrical sensing module 86 may additionally or alternatively provide digitized ECG signals to cardiac signal analyzer 120 for use in detecting tachyarrhythmias. Examples of ICDs that may be adapted for use with a triggered pacemaker 100 and operations that may be performed by tachyarrhythmia detector 94 for detecting, discriminating and treating tachyarrhythmia are generally disclosed in U.S. Pat. No. 7,742,812 (Ghanem, et al.), U.S. Pat. No. 8,160,684 (Ghanem, et al.), U.S. Pat. No. 5,354,316 (Keimel); U.S. Pat. No. 6,393,316

(Gillberg et al.), U.S. Pat. No. 5,545,186 (Olson, et al.), and U.S. Pat. No. 5,855,593 (Olson, et al.), all of which patents are incorporated herein by reference in their entirety.

The detection algorithms are highly sensitive and specific for the presence or absence of life threatening VT and VF. Therapy delivery module 84 includes a HV therapy delivery module including one or more HV output capacitors. When a malignant tachycardia is detected the HV capacitors are charged to a pre-programmed voltage level by a HV charging circuit. Control module 80 applies a signal to trigger discharge of the HV capacitors upon detecting a feedback signal from therapy delivery module 84 that the HV capacitors have reached the voltage required to deliver a pro-grammed shock energy. In this way, control module 80 controls operation of the high voltage output circuit of therapy delivery module 84 to deliver high energy cardioversion/defibrillation shocks using coil electrode 24 and housing electrode 15.

It should be noted that implemented arrhythmia detection algorithms may utilize not only ECG signal analysis methods but may also utilize supplemental sensors 96, such as tissue color, tissue oxygenation, respiration, patient activity, heart sounds, and the like, for contributing to a decision by processing and control module 80 to apply or withhold a therapy. Sensors 96 may also be used in determining the need for pacing and timing of pacing pulses by pacemaker 100. For example, an activity sensor signal or other rate responsive signal, such as a minute ventilation signal, may be used for determining a pacing rate meeting a patient's metabolic demand. Timing circuit 92 produces a control signal 95 to cause emitting device 18 to generate optical trigger signals that cause pacemaker 100 to deliver pacing pulses at a rate based on the rate responsive signal. Sensors 96 may include one or more sensors carried by a lead extending from ICD 14, within or along housing 15, and/or connector block 13.

Telemetry module 88 includes a transceiver and antenna for communicating with another device, such as an external programmer 40 and emitting device 18 when it is configured as a wireless device. Under the control of control processor 80, telemetry module 88 may receive downlink telemetry from and send uplink telemetry to programmer 40 or other external device. Telemetry module 88 may transmit a control signal 95 wirelessly to emitting device 18, e.g., as an RF signal.

Figure 6A:
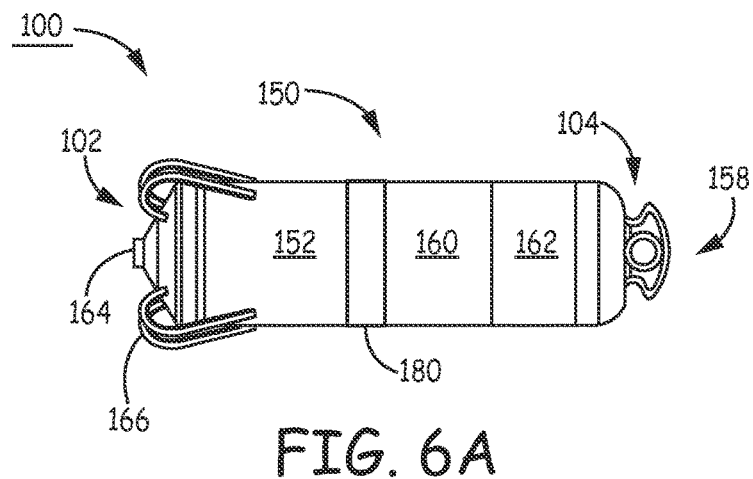
FIG. 6A is a conceptual diagram of a triggered pacemaker included in the system shown in FIG. 2.

FIG. 6A is a conceptual diagram of triggered pacemaker 100. Pacemaker 100 includes electrodes 162 and 164 spaced apart along the housing 150 of pacemaker 100. Electrode 164 is shown as a tip electrode extending from a distal end 102 of pacemaker 100, and electrode 162 is shown as a ring electrode along a mid-portion of housing 150, for example adjacent proximal end 104. In alternative embodiments, pacemaker 100 may include two or more ring electrodes or other types of electrodes exposed along pacemaker housing 150 for delivering electrical stimulation to heart 26. Electrodes 162 and 164 may be, without limitation, titanium, platinum, iridium or alloys thereof and may include a low polarizing coating, such as titanium nitride, iridium oxide, ruthenium oxide, platinum black among others. Electrodes 162 and 164 may be positioned at locations along pacemaker 100 other than the locations shown.

The housing 150 includes a control electronics subassembly 152, which houses the electronics for producing stimulation pulses and controlling therapy delivery functions of pacemaker 100. As one example, control electronics subassembly 152 may include a pulse generator and a light detector for receiving an optical trigger signal and triggering the pulse generator to deliver a pacing pulse via electrodes 162 and 164 in response to the optical trigger signal.

Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety. Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162 and 164 uninsulated. In other examples, the entirety of the housing 150 may function as an electrode instead of providing a localized electrode such as electrode 162. Alternatively, electrode 162 may be electrically isolated from the other portions of the housing 150. Electrodes 162 and 164 form an anode and cathode pair for bipolar cardiac pacing. In some embodiments, electrodes 162 and 164 may be used for sensing cardiac EGM signals, in which case control electronics subassembly 152 includes sensing circuitry.

Pacemaker 100 may include a set of active fixation tines 166 to secure pacemaker 100 to patient tissue, e.g. by interacting with the ventricular trabeculae. Pacemaker 100 may include a set of active fixation tines as disclosed in commonly-assigned, pre-grant publication U.S. 2012/0172892 (Grubac, et al.), hereby incorporated herein by reference in its entirety. Fixation tines 166 are configured to anchor pacemaker 100 to position electrode 164 in operative proximity to a targeted tissue for delivering electrical stimulation pulses. Numerous types of active and/or passive fixation members may be employed for anchoring or stabilizing pacemaker 100 in an implant position.

Pacemaker 100 may further include a delivery tool interface 158. Delivery tool interface 158 is located at the proximal end of pacemaker 100 and is configured to connect to a delivery device, such as a catheter, used to position pacemaker 100 at an implant location during an implantation procedure, for example within a heart chamber.

Pacemaker 100 includes an optical coupling window 180 for receiving and coupling an optical trigger signal from an optical signal emitting device 18 to a light detector enclosed within housing 150. Window 180 may include silica, quartz, sapphire, or other transparent light conducting material for transmitting the optical trigger signal to a light detector without significant light scattering. In one example, window 180 is a sapphire ring that is gold brazed to the control electronics subassembly 152, either directly or using a titanium ferrule that is welded to the control electronics subassembly, and to the battery assembly, either directly or indirectly using a second titanium ferrule that is welded to the battery subassembly 160. In another example, window 180 may be fusion bonded to housing 150, with or without the use of an intervening metallic ferrule. For examples of materials and methods for forming optical windows in an IMD, reference is made to commonly assigned U.S. Pat. No. 8,275,432 (Kuhn, et al.) and U.S. Pat. No. 5,902,326 (Lessar et al.). The entirety of both patents is incorporated herein by reference.

A light detector included in control electronics subassembly 152 receives light incident on pacemaker 100 through window 180. When pacemaker 100 is advanced transvenously into a heart chamber, the final orientation of pacemaker 100 may vary and the final orientation of optical window 180 relative to the patient's anatomy, and therefore relative to emitting device 18 may be unknown. Furthermore, the orientation of optical window 180 relative to the emitting device 18 may fluctuate over time due to shifting of either pacemaker 100 and/or emitting device 18 or due to cardiac motion, respiratory motion, or other body motion. As such, window 180 may be a continuous window circumscribing housing 150 to receive light from all sides of pacemaker 100.

In other embodiments window 180 may be discontinuous and include multiple segmented windows along the circumference of housing 150. It is contemplated that numerous configurations for one or more optical windows along distal end 102, proximal end 104 or along the circumference of housing 150, e.g., along the cylindrical longitudinal sidewall extending between the proximal and distal ends 102 and 104, may be conceived. In yet other embodiments, housing 150 or portions thereof, may be formed of a transparent light conducting material, such as a wafer-scale glass package, such that a light detector enclosed within housing 150 may receive light directly through housing 150 without requiring a separate optical window. A wafer-scale package that may be used to house the light detector of pacemaker 100 and/or the emitting device 18 within the sensing device (e.g., sensing device 4 or ICD 14) is generally disclosed in commonly-assigned U.S. Pat. No. 8,666,505 (O'Brien, et al.), hereby incorporated herein by reference in its entirety.

Figure 6B:
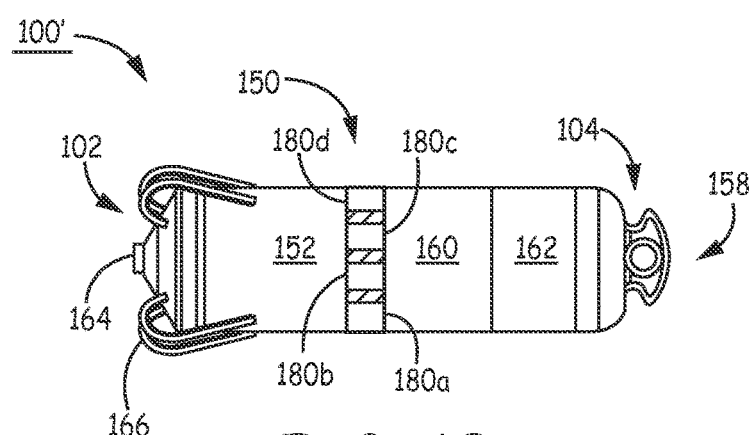
FIG. 6B is a conceptual diagram of a triggered pacemaker according to an alternative embodiment.

FIG. 6B is a conceptual diagram of pacemaker 100 according to an alternative embodiment. Instead of a continuous circumferential window 180 as shown in FIG. 6A, multiple discrete optical coupling windows 180a through 180d may be distributed along multiple sides of pacemaker 100. Pacemaker 100 is shown having a generally cylindrical housing 150 in FIGS. 6A and 6B. In other embodiments, pacemaker 100 may have a prismatic housing including one continuous or multiple discrete optical coupling windows extending along one or more sides of the housing 150.

The optical coupling windows 180a through 180d may be formed of silica, quartz, sapphire, or other optically transparent material as described above. A light detector may be positioned behind each of the optical windows 180a through 180d. When multiple light detectors are included, a single light detector producing the greatest voltage signal due to incident light may be selected through switching circuitry as the light detector used to detect an optical trigger signal for causing the pacemaker 100 to deliver a pacing pulse. Alternatively, the output signal of a combination of light detectors may be used in a logical OR or AND operation for the detection of the optical trigger signal.

Figure 6C:
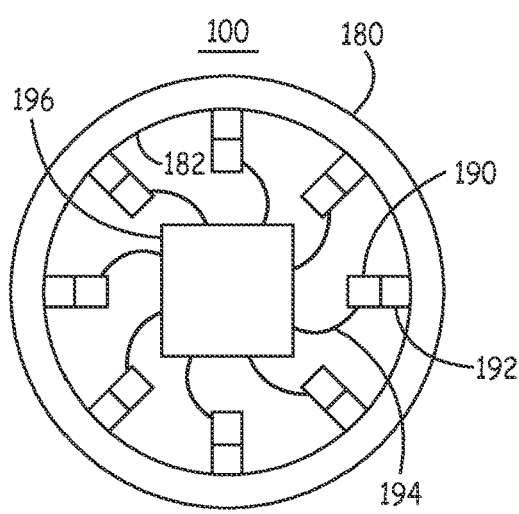
FIG. 6C is a sectional view of the pacemaker shown in FIG. 6A.

FIG. 6C is a sectional view of pacemaker 100 along optical coupling window 180. Window 180 is shown as continuous ring, e.g. of sapphire or other light transmitting material. A photosensitive component 190, e.g. a photoresistor, photodiode, or other photodetector, is mounted along an interior surface 182 of window 180. Photosensitive component 190 may be coupled to surface 182 via an optional optical coupling member 192 or may be potted in a coupling member 192 that is sealed to surface 182. Optical coupling member 192 may be configured as generally disclosed in the above-incorporated '432 patent. While interior surface 182 and exterior surface 184 of window 180 are shown to be circular, surface 182 and 184 may include flat portions or facets where photosensitive components 190 are coupled to surface 182 to reduce light scattering at the curved surfaces.

Each photosensitive component 190 is electrically coupled to a hybrid circuit 196 via conductors 194. Hybrid circuit 196 receives electrical signals from each of photosensitive components 190 when light is received through window 180 from any side of pacemaker 100 and compares the electrical signals, individually or in combination, to a trigger detection threshold as described in greater detail below.

Figure 7A:
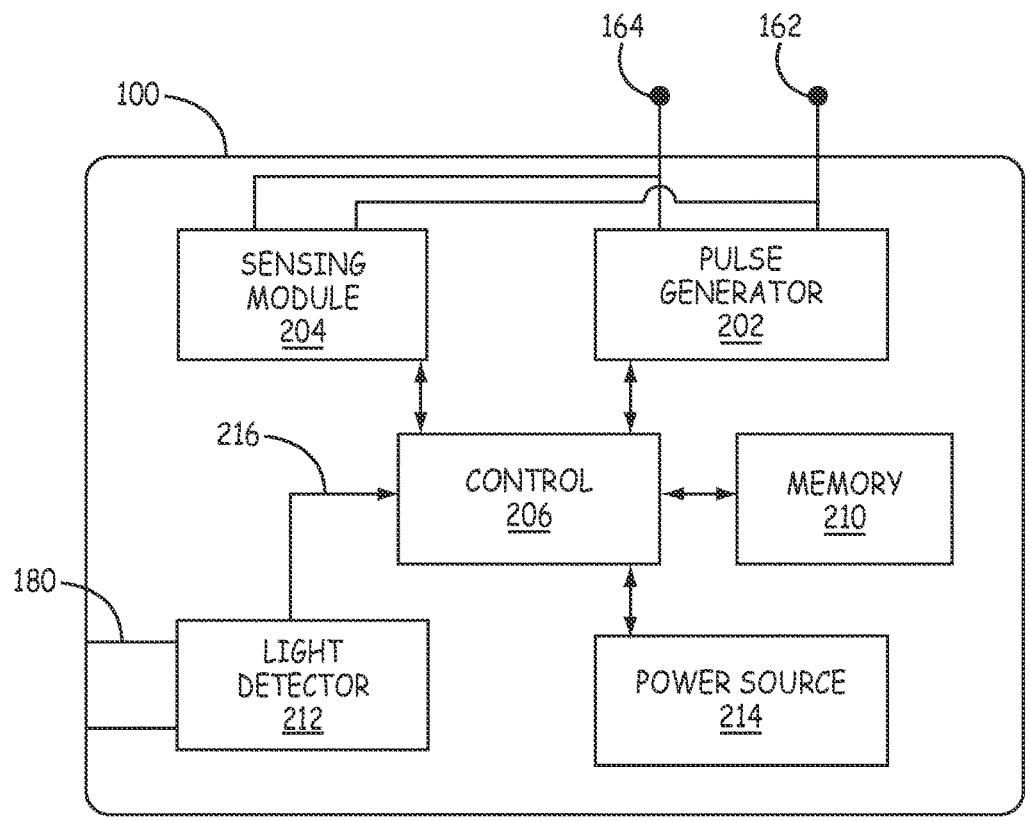
FIG. 7A is a functional block diagram of the pacemaker of FIG. 2A according to one example.

FIG. 7A is a functional block diagram of an example configuration of a pacemaker. Pacemaker 100 includes a pulse generator 202, a sensing module 204, a control module 206, memory 210, light detector 212 and a power source 214. Pulse generator 202 generates electrical stimulation pulses that are delivered to heart tissue via electrodes 160 and 162. Control module 206 controls pulse generator 202 to deliver a stimulation pulse in response to receiving a trigger detect signal 216 from light detector 212. In other embodiments, pulse generator 202 may be enabled to deliver a stimulation pulse directly by a trigger detect signal 216 received from light detector 212. For example, a switch responsive to a trigger detect signal 216 produced by light detector 212 may enable pulse generator 202 to produce a stimulation pulse that is applied to electrodes 162 and 164.

Pulse generator 202 includes one or more capacitors and a charging circuit to charge the capacitor(s) to a pacing pulse voltage under the control of control module 206. The pacing capacitor may be charged to the pacing pulse voltage while control module 206 waits for a trigger detect signal 216 from light detector 212. Upon detecting the optical trigger signal, the pacing capacitor(s) is coupled to pacing electrodes 162, 164 to at least partially discharge the capacitor voltage and thereby deliver the pacing pulse. Alternatively, detection of the optical trigger signal initiates pacing capacitor charging and when a predetermined capacitor voltage is reached, the pulse is delivered. Pacing circuitry generally disclosed in U.S. Pat. No. 8,532,785 (Crutchfield, et al.), hereby incorporated herein by reference in its entirety, may be implemented in pacemaker 100 for charging a pacing capacitor to a predetermined pacing pulse amplitude under the control of control module 202 and delivering a pacing pulse. Alternatively, pulse generator 202 may include a switch that connects power source 214 to pacing electrodes 162 and 164 to deliver the pacing pulse.

Light detector 212 receives light through optical coupling window 180. Light detector 212 includes one or more optical transducers which may include, without limitation, a photodetector, photodiode, photoresistor, photomultiplier, PIN diode, avalanche diode or other light sensitive optoelectronic component that is responsive to a light wavelength emitted by emitting device 18. One or more optical transducers included in light detector 212 are selected to minimize power consumption in the pacemaker 100 used for optical trigger signal detection. Upon receiving the optical trigger signal coupled to light detector 212 via window 180, light detector 212 produces a voltage signal that is compared to a trigger detection threshold. When the voltage signal exceeds the trigger detection threshold, the trigger detect signal 216 is passed to control module 206.

In one embodiment, emitting device 18 may be configured to emit an optical trigger signal having a center wavelength of 1100 nm. In this example, an Indium-Gallium-Arsenide photodetector may be used to provide efficient sensing of the 1100 nm trigger signal. An example of an Indium-Gallium-Arsenide photodetector is available from Sensors Unlimited, Inc., Princeton, N.J., USA. Semiconductor materials used in light detector 212 may include, without limitation, lead sulfide, lead selenide, indium arsenide, gallium arsenide, indium antimonite, aluminum antimonite, germanium, silicon, or combinations thereof.

Light detector 212 may include multiple optical transducers positioned to receive light through one or more light receiving windows 180, for example along one or more sides of pacemaker 100. In some embodiments, window 180 is a continuous ring circumscribing a cylindrical pacemaker as shown in FIG. 6A. Multiple optical transducers may be positioned along the interior surface of the window to produce a voltage signal that is compared by a comparator included in light detector 212 to a trigger detection signal. The voltage signal produced by multiple optical transducers may be summed, for example, for comparison to a trigger signal detection threshold or the largest voltage signal produced by an optical transducer may be compared to the detection threshold.

In some embodiments, multiple optical transducers may be included in light detector 212 that are responsive to different wavelengths. Providing detection of different wavelengths may enable different trigger signals to be transmitted by emitting device 18 for causing pacemaker 100 to perform different pacing functions. The light detector 212 may be configured to detect only the device-generated optical trigger signal from emitting device 18 in some embodiments. In other words, light detector 212 may not be configured to sense and process physiological optical signals for determining a physiological event, condition or state In examples that include multiple therapy delivery devices, e.g., as shown in FIG. 4B, each light detector 212 may include multiple selectable photosensitive components, including one or more photodetectors, one or more photodiodes, one or more photoresistors, etc., for sensing optical trigger signals at different wavelengths. At the time of implantation, a trigger signal wavelength is selected and programmed into memory 210. The photosensitive component that is sensitive to the selected wavelength is enabled, and other photosensitive components are disabled. In this way, the light detector 212 may be configured for detecting the selected trigger signal wavelength so that pacemaker 100 responds to specific optical trigger signals matching the selected wavelength but does not respond to trigger signals of other wavelengths.

A light detector 212 that is selectably responsive to different wavelengths may also allow different wavelengths to be selected in order to optimize a signal to noise ratio for detecting the optical trigger signal. In some cases, one wavelength may be more attenuated than other available wavelengths.

Providing multiple photosensitive components sensitive to different wavelengths further allows pacemakers 100 to be manufactured with identical components but later be configured to be responsive to different trigger signal wavelengths, e.g. at the time of implantation. Alternatively, pacemaker 100 may be manufactured with different light detectors 212 that are responsive to different trigger signals without a selectable detection wavelength.

Light detector 212 produces a trigger detect signal 216 received by control module 206 or directly by pulse generator 202. Control module 206 then controls pulse generator 202 to deliver a pacing pulse according to therapy delivery control parameters such as pulse amplitude, pulse width, pulse number, etc., which may be stored in memory 210. In some examples, pulse generator 202 is enabled to deliver a pacing pulse immediately upon receiving the trigger detect signal 216, either directly from light detector 212 or via control module 206. In other examples, pulse generator 202 delivers the pacing pulse after a time delay between receiving trigger detect signal 216 as controlled by control module 206.

Pacemaker 100 may be solely a therapy delivery device without sensing capabilities. In other examples, pacemaker 100 may include a sensing module 204 coupled to electrodes 162 and 164 for sensing near-field EGM signals for use in controlling the delivery of pacing pulses. For example, when pacemaker 100 is implanted in the LV, R-waves in the LV may be sensed by sensing module 204. Sensing module 204 generates an R-wave sense event signal that is provided to control module 206. Control module 206 may start a pacing timing interval upon receiving a trigger detect signal 216 from light detector 212. If an R-wave sense signal is received by control module 206 from sensing module 204 prior to the pacing timing interval expiring, no pacing pulse is delivered. If the pacing timing interval expires prior to receiving an R-wave sense event signal from sensing module 204, control module 206 enables pulse generator 202 to deliver a pacing pulse.

The pacing timing interval may be, for example, a VV interval to control delivery of a pacing pulse to the LV (or RV) relative to an intrinsic R-wave sensed by sensing device 4 or ICD 14. The pacing timing interval may be an AV interval to control delivery of a pacing pulse in a ventricle relative to an intrinsic P-wave sensed by sensing device 4 or ICD 14. The pacing timing interval may be relative to a pacing pulse that is delivered in another heart chamber that may also be delivered by another intracardiac pacemaker that is triggered to deliver a pacing pulse by an optical trigger signal from emitting device 18. For example, ICD 14 may control emitting device 18 to produce an optical trigger signal. A pacing pulse may be delivered in one heart chamber by a first intracardiac pacemaker immediately upon receiving the optical trigger signal. A pacing pulse in a second heart chamber may be delivered upon expiration of a pacing timing interval that is started upon receiving the optical trigger signal as long as the sensing module 204 does not produce an intrinsic sensed event signal prior to the expiration of the pacing timing interval.

While not shown in FIG. 7A, it is recognized that pacemaker 100 may include other physiological sensors, such as a pressure sensor, activity sensor, acoustical sensor, oxygen sensor, or other sensor adapted for use in an implantable medical device.

Power source 214 provides power to each of the other modules and components of pacemaker 100 as required. Control module 206 may execute power control operations to control when various components or modules are powered to perform various pacemaker functions. Power source 214 may include one or more energy storage devices, such as one or more rechargeable or non-rechargeable batteries. Control module 206 may also be configured to perform diagnostic testing of pacemaker 100, which may include monitoring the remaining charge of power source 214. The connections between power source 214 and other pacemaker modules and components are not shown in FIG. 7A for the sake of clarity.

Circuitry represented by the block diagram shown in FIG. 7A may include any discrete and/or integrated electronic circuit components that implement analog and/or digital circuits capable of producing the functions attributed to pacemaker 100 herein. The functions attributed to pacemaker 100 herein may be embodied as one or more processors, hardware, firmware, software, or any combination thereof. Control module 206 may include any one or more of a microprocessor, a controller, a digital signal processor (DSP), an application specific integrated circuit (ASIC), a field-programmable gate array (FPGA), or equivalent discrete or integrated logic circuitry. Depiction of different features of pacemaker 100 as discrete modules or components is intended to highlight different functional aspects and does not necessarily imply that such modules must be realized by separate hardware or software components. Rather, functionality associated with one or more modules may be performed by separate hardware or software components, or integrated within common or separate hardware or software components, which may include combinational or sequential logic circuits, state machines, memory devices, etc.

Memory 210 may include computer-readable instructions that, when executed by control module 206, cause control module 206 to perform various functions attributed throughout this disclosure to pacemaker 100. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 210 stores intervals, counters, or other data used by control module 206 to control the delivery of pacing pulses by pulse generator 202 in response to a trigger detect signal 216 received from light detector 212.

Figure 7B:
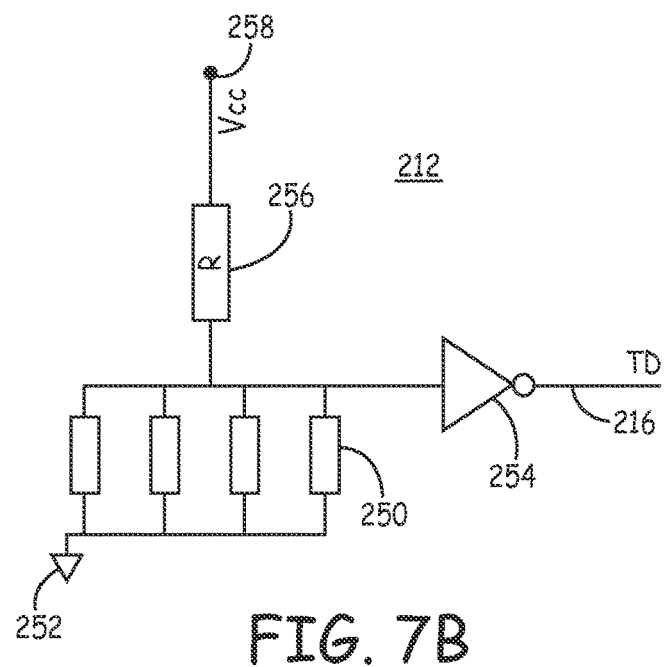
FIG. 7B is a diagram of one example of a light detector included in the pacemaker of FIG. 7A.

FIG. 7B is a diagram of one example of a light detector 212 included in the pacemaker of FIG. 7A. Multiple photosensitive components 250 may be coupled in parallel between an input of a digital inverter 254 and ground 252. In one example, photosensitive components 250 are photoresistors. The input of the digital inverter 254 is biased to Vcc 258 through a resistor 256 having a high resistance that is less than the resistance of the photoresistors 250 when no light is being received. When an optical trigger signal is being received, through window 180, the resistance of one or more photoresistors 250 will decrease significantly, switching the state of the digital inverter 254. An output signal of the digital inverter 254 may be provided as the trigger detect signal 216 to control module 206. Photoresistors 250 may be arranged along a window 180 that circumscribes pacemaker 100 to achieve optical trigger signal reception from 360 degrees, as shown in FIG. 6C. While four photoresistors 250 are shown in FIG. 7B, it is recognized that one or more photoresistors or other photosensitive components may be included in light detector 212.

Figure 8A:
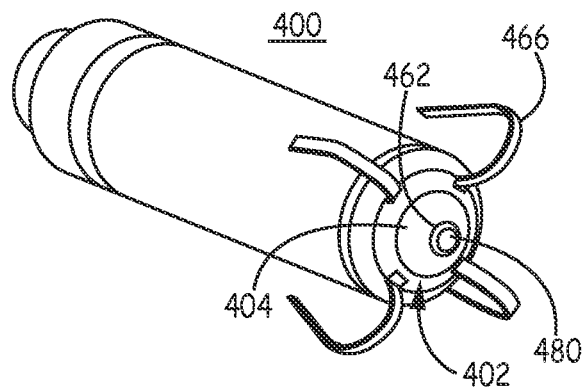
FIG. 8A is a conceptual diagram of an optically-triggered therapy delivery device, shown as an intracardiac pacemaker.

FIG. 8A is a conceptual diagram of yet another example of an optically triggered therapy delivery device, shown as intracardiac pacemaker 400. Pacemaker 400 has a distal face 402 having a tip electrode 462 retained in an aperture of an insulating electrode feedthrough 404. Tip electrode 462 is in the form of a ring electrode having an open center in which optical window 480 resides. Window 480 may be formed of any of the example materials listed previously herein and may be sealed within tip electrode 462 by a gold braze, medical adhesive, fusion bonding or other sealing methods. Tip electrode 462 is a ring-shaped electrode with the optical window 480 extending co-axially through the center of tip electrode 462. A light detector 212 is positioned directly behind the window 480 for receiving the optical trigger signal. Tip electrode 462 may be increased in diameter such that window 480 may encompass a larger surface area of the distal face 402 of pacemaker 400.

Tip electrode 462 is urged against or proximate the heart chamber wall by fixation tines 466. As such, distal face 402 will be oriented in a generally outward direction from the heart chamber blood pool, toward the thoracic wall. Optical coupling window 480 is positioned against or near the myocardial wall providing an optical path from an emitting device directly toward window 480, e.g. through intercostal muscle, lung tissue and the myocardial wall.

Figure 8B:
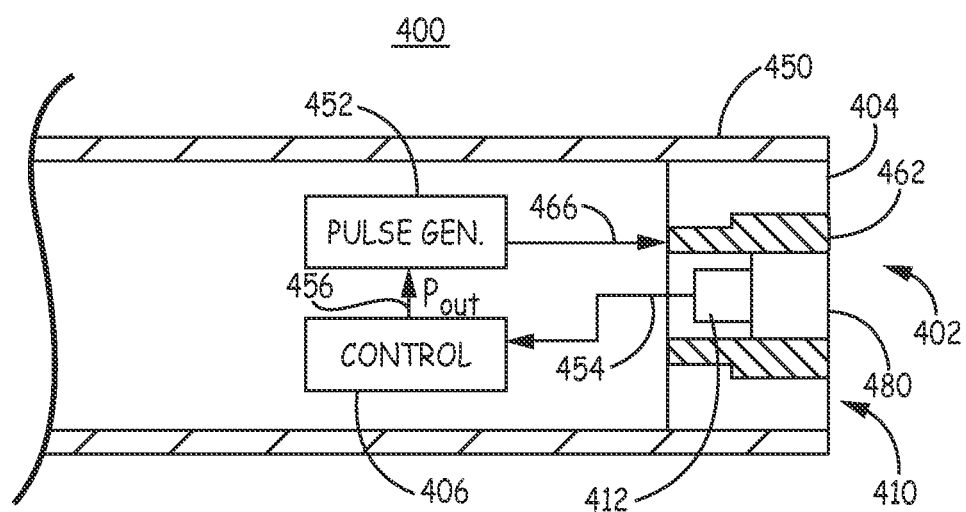
FIG. 8B is a conceptual, side, sectional view of the pacemaker shown in FIG. 8A.

FIG. 8B is a conceptual, side, sectional view of the pacemaker 400 shown in FIG. 8A. Pacemaker 400 includes housing 450 and an electrode and light detector assembly 410 exposed along the distal end face 402 of pacemaker 400. Electrode and light detector assembly 402 includes electrode feedthrough 404, tip electrode 462, optical coupling window 480 and light detector 412. Pulse generator 452 is electrically coupled to electrode 462 via a feedthrough conductor 466. Tip electrode 462 has a hollow core in which transparent optical window 480 is positioned for passing an optical trigger signal to light detector 412. Light detector 412 is shown positioned in the hollow core of tip electrode 462 however depending the relative sizes of detector 412 and electrode 462, it is recognized that light detector 412 may be positioned in a more proximal position relative to distal tip electrode 462. In this case, optical window 480 may fill the hollow core of electrode 462. Assembly 410 may be pre-assembled prior to assembling with housing 450. Alternatively, the feedthrough 404, electrode 462, light detector 412 and window 480 may be assembled into housing 450 individually or in sub-assemblies. The assembly 410 and housing 450 are sealed to inhibit the ingress of body fluids to the interior of pacemaker 400 using brazing, welding, medical-grade adhesive or combination thereof and/or other sealing methods.

A trigger detection threshold applied to light detector 412 may be set and stored in memory for use in detecting an optical trigger signal. When light detector 412 produces a trigger detect signal 454, control module 406 passes a Pout signal 456 to pulse generator 452. Pulse generator 452 delivers one or more pacing pulses via electrode 462 and a return anode electrode, e.g., a ring electrode (not shown) around housing 450 or any portion or the entirety of housing 450) in response to the Pout signal from control module 406. Pulse generator 452 generates the one or more pacing pulse according to stored pacing pulse parameters (e.g. pulse amplitude, pulse width, pulse shape, etc.). As long as the trigger detect signal 454 remains low or below the trigger detection threshold, no pacing pulses are delivered.

In some examples, control module 406 may pass the Pout signal 456 to cause pacing pulse delivery immediately upon a trigger detect signal 454. In other examples, control module 406 passes the Pout signal 456 after a stored time delay, such as an atrioventricular (AV) or ventricular-ventricular (VV) delay or portion thereof used to control dual chamber or multi-chamber bradycardia pacing or CRT.

Figure 9A:
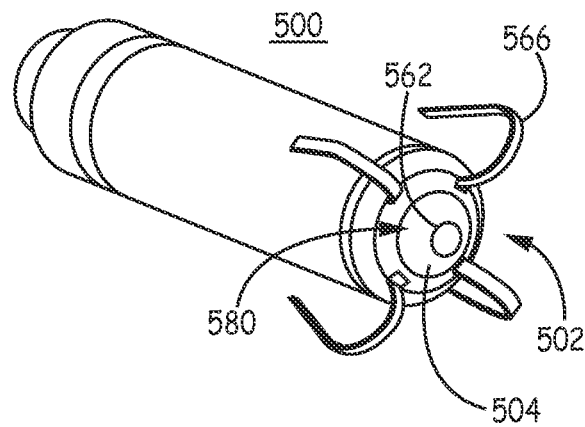
FIG. 9A is a conceptual diagram of an alternative example of a pacemaker.

FIG. 9A is a conceptual diagram of an alternative example of a pacemaker 500 having an optical coupling window 580 encircling tip electrode 562 along a distal face 502 of pacemaker 500. Optical window 580 may be a portion of the insulating electrode feedthrough 504 surrounding tip electrode 562. Electrode feedthrough 504 may include a glass insulating member that is transparent and serves to conduct light to a light detector 512 (shown in FIG. 9B) positioned along an internal surface of the feedthrough 504. Alternatively, optical window 580 may be a glass or other transparent ring encircling the feedthrough 504 surrounding tip electrode 562. In this case optical window 580 may be a ring-shaped window that extends co-axially around tip electrode 562.

Figure 9B:
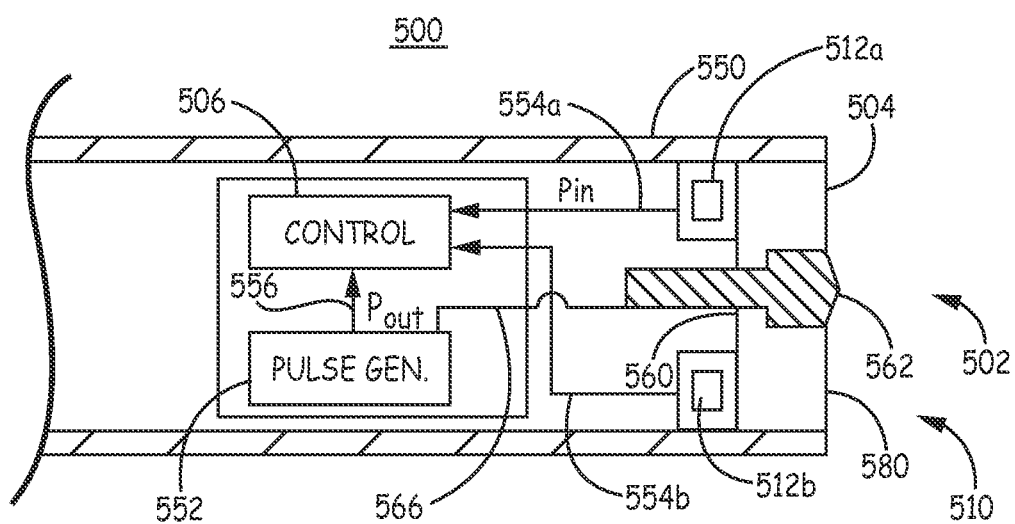
FIG. 9B is a conceptual, side, sectional view of the pacemaker shown in FIG. 9A.

FIG. 9B is a conceptual, side, sectional view of the pacemaker 500 shown in FIG. 9A. Pacemaker 500 includes housing 550 and an electrode and light detector assembly 510 exposed along the distal end face 502 of pacemaker 500. Electrode and light detector assembly 502 includes electrode feedthrough 504, tip electrode 562, optical window 580 and light detectors 512a and 512b, collectively 512. While two detectors 512 are shown, it is recognized that one or more detectors may be positioned along the interior surface 560 of window 580. Tip electrode 562 is a solid tip electrode in this example, insulated from housing 550 by a glass insulator member of feedthrough 504 and electrically coupled to pulse generator 552 by feedthrough conductor 566.

Feedthrough 504 includes window 580 which is a glass electrical insulator member of feedthrough 504 and an optical window for passing an optical trigger signal to light detectors 512. Assembly 510 may be pre-assembled prior to assembling with housing 550. Alternatively, the feedthrough 504, electrode 562, and light detectors 512 may be assembled into housing 550 individually or in sub-assemblies. The assembly 510 and housing 550 are sealed to inhibit the ingress of body fluids to the interior of pacemaker 500 using brazing, welding, medical-grade adhesive or combination thereof and/or other sealing methods.

Control module 506 receives light detector signals 554a and 554b from light detectors 512. In this case, control module 506 may include a comparator or other detection circuitry for comparing the signals 554a and 554b to a trigger detect threshold. Control module 506 may select one or both of light detector signals 554a and 554b for detecting the optical trigger signal. A selected one or both of trigger detect signals 554a and 554b may be compared to a trigger detect threshold or a sum or other combination of the trigger detect signals 554a and 554b may be compared to a pace trigger threshold. Control module 506 is coupled to the pulse generator 552 via Pout signal line 556 for controlling the pulse generator 552 to deliver pacing pulses via electrode 562 and a return anode electrode, e.g., a ring electrode, not shown, around housing 550 or any portion or the entirety of housing 550). If the trigger detect signals 554a and/or 554b or combination thereof crosses the trigger detect threshold, control module 506 passes a Pout signal 556 to pulse generator 552. Upon receiving the Pout signal 556, pulse generator 552 generates one or more pacing pulses as described above.

Figure 10:
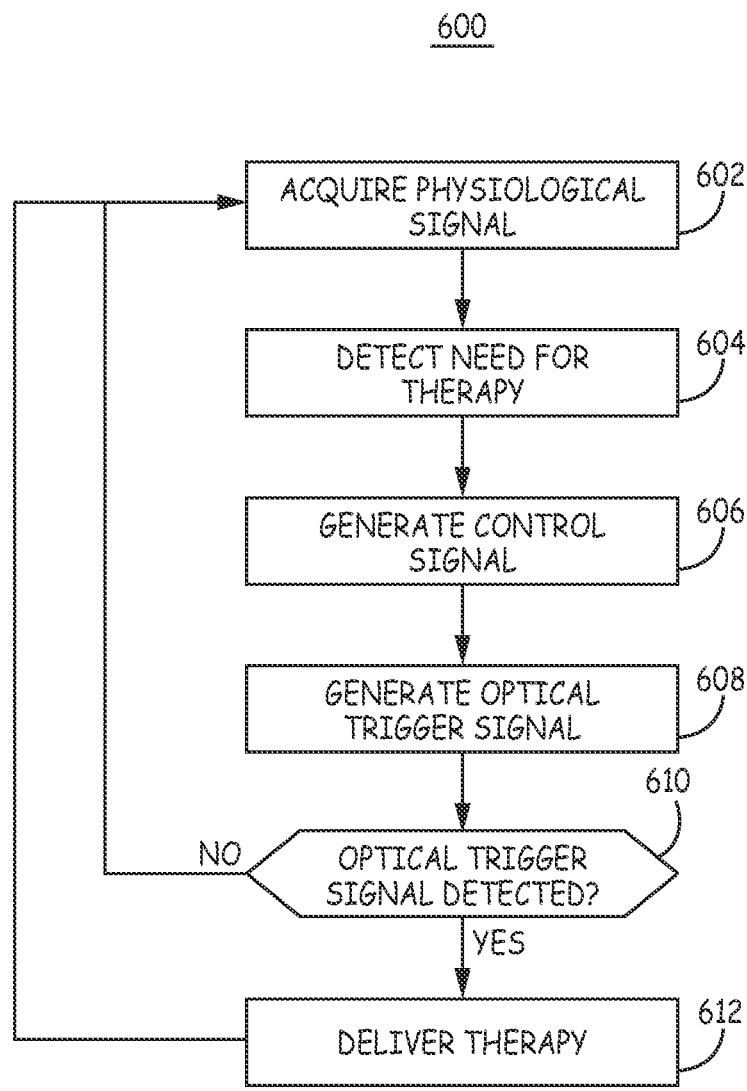
FIG. 10 is a flow chart of a method for controlling a therapy delivery device according to one example.

FIG. 10 is a flow chart 600 of a method for controlling a triggered therapy delivery device according to one example. The method shown in flow chart 600 and other flow charts presented herein may be performed by any of the systems 2, 10, 10', 10" or 11 shown in FIG. 1A, 2A, 4A or 4B. At block 602, a sensing device, e.g., sensing device 4 or ICD 14, acquires a physiological signal for sensing events or conditions that indicate a need for automatic therapy delivery. The sensing device detects a need for therapy, at block 604, based on the physiological signal. The sensing device need not be directly electrically coupled to the triggered therapy delivery device. The sensing device generates a control signal at block 606 that is passed directly to a light emitting device that is in wired connection with the sensing device. Alternatively the sensing device generates a control signal that is encoded by a telemetry communication module of the sensing device and transmitted wirelessly to the light emitting device at block 606.

The light emitting device generates an optical trigger signal at block 608 in response to receiving the control signal. The triggered therapy delivery device, e.g., therapy delivery device 6 or pacemaker 100, detects the optical trigger signal at block 610. In response to detecting the optical trigger signal, a therapy is automatically delivered at block 612. If no optical trigger signal is being detected, no therapy is delivered. After delivering the therapy, the sensing device continues to monitor the physiological signal at block 602.

Figure 11:
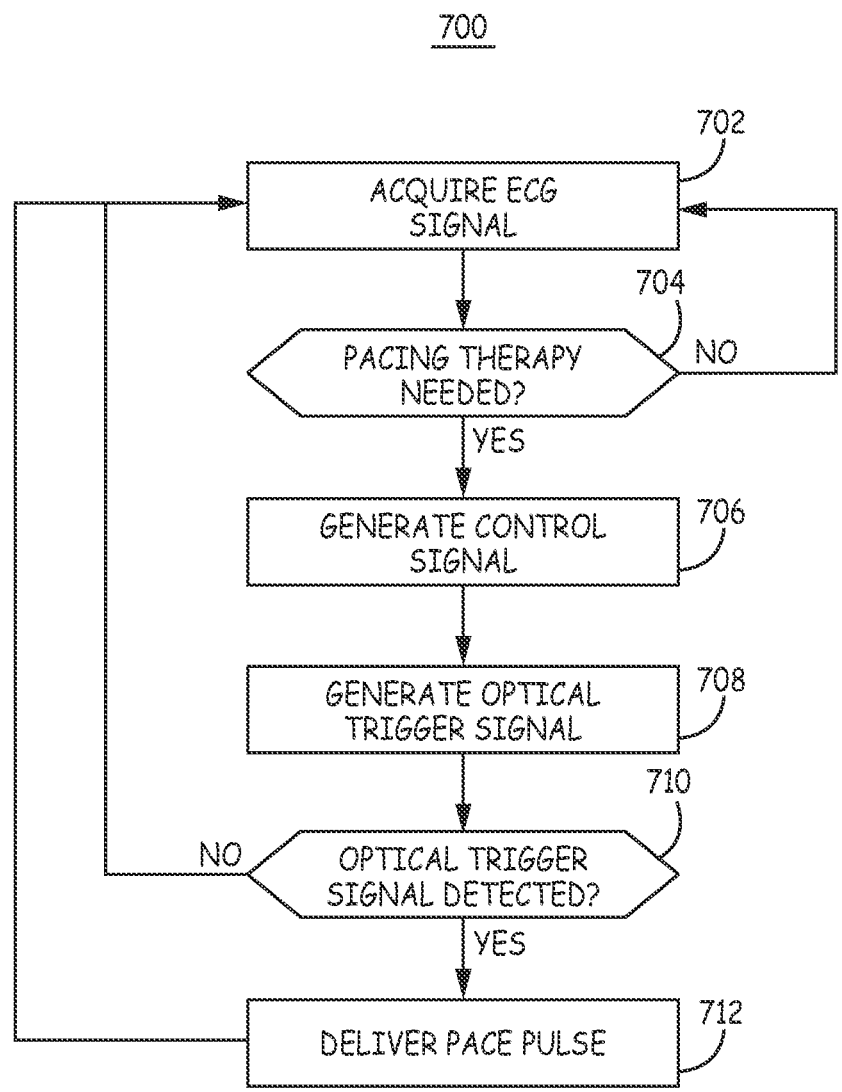
FIG. 11 is a flow chart of a method for controlling a cardiac pacing therapy automatically delivered by an intracardiac pacemaker.

FIG. 11 is a flow chart 700 of a method for controlling a cardiac pacing therapy automatically delivered by a triggered pacemaker, e.g., pacemaker 100. The sensing device, e.g., sensing-only device 4 or ICD 14, acquires an ECG signal at block 702. The sensing device may be configured as a sensing-only device (e.g. as shown in FIG. 1B) for monitoring the ECG signal using electrodes carried on the sensing device or a lead extending from the sensing device. The sensing device may or may not be capable of delivering a therapy. In one example, the sensing device includes cardioversion/defibrillation capabilities for treating tachyarrhythmias. As described above, the sensing device may be an ICD configured to monitor the ECG to detect a need for pacing and for detecting VT and VF and delivering shock therapies as needed. The sensing device may be an extrathoracic device, e.g. implanted in a subcutaneous or submuscular pocket, or an intrathoracic device and need not be in wired connection with the pacemaker 100.

If a pacing therapy is needed, as determined at block 704 based on the sensed ECG signal, a control signal is generated by the sensing device at block 706. The control signal may be an electrical signal passed directly to the optical emitting device, either through a wired connection or via conversion and transmission of a wireless telemetry signal such as an RF communication signal.

The optical emitting device, for example emitting device 18, generates an optical trigger signal at block 708 in response to receiving the control signal from the sensing device. If the pacemaker 100 detects the optical trigger signal, as determined at block 710, one or more pacing pulses are delivered at block 712 in response to the trigger signal detection. If no optical trigger signal is detected, the sensing device continues monitoring the ECG signal for the need for a pacing pulse(s). The pacing pulses may be delivered according to pacing pulse control parameters stored by the control module of the pacemaker or may be adjusted according to the detected trigger signal.

Figure 12:
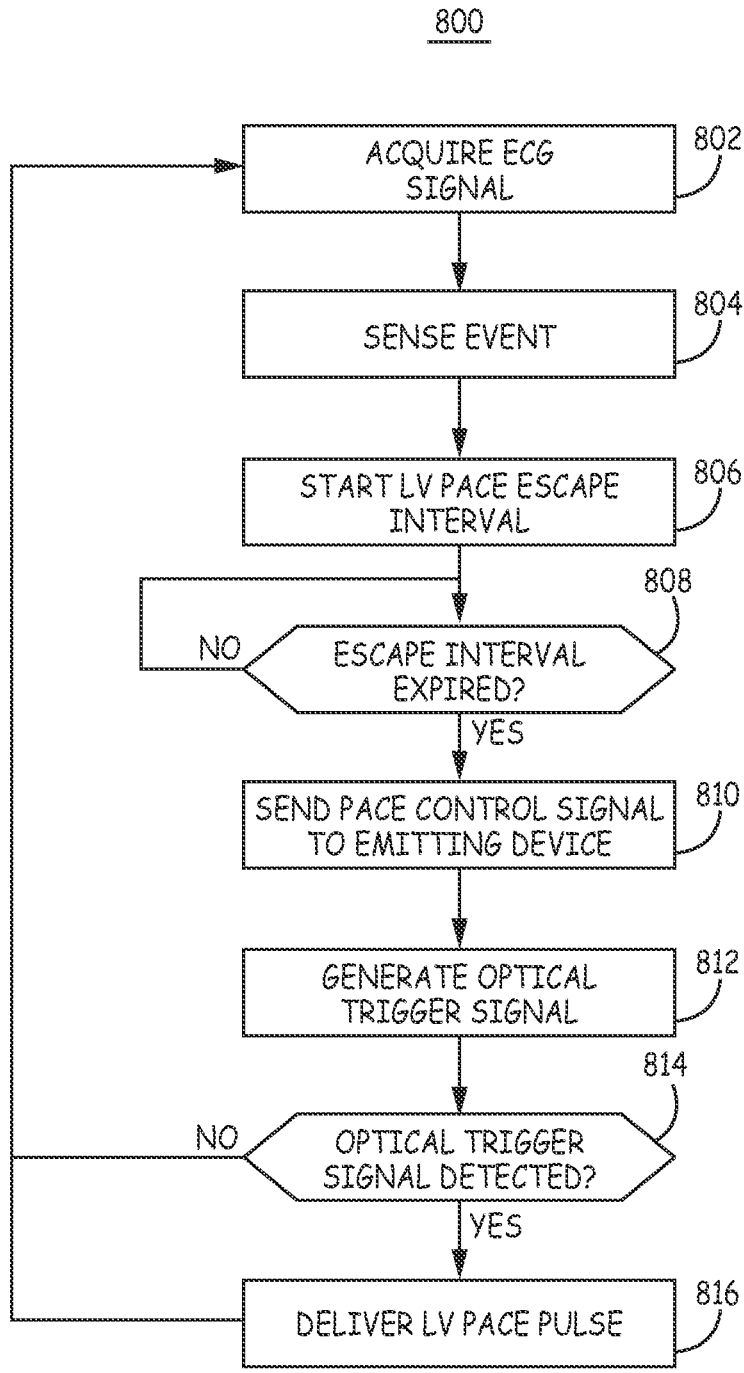
FIG. 12 is a flow chart of a method for controlling CRT according to one embodiment.

FIG. 12 is a flow chart 800 of a method for controlling cardiac resynchronization therapy (CRT) according to one embodiment. At block 802, a sensing device receives an ECG signal for sensing P-waves and/or R-waves attendant to the depolarization of the atria and the ventricles, respectively. The sensing device may be a sensing-only device 4 as shown in FIG. 1B or an ICD 14, e.g. as shown in FIGS. 2A, 3A, 3B and 4A. A timing event, i.e. a P-wave or an R-wave, is sensed at block 804 causing a pacing escape interval to be started in the sensing device. In the example shown, an LV pacing escape interval is started at block 806. The LV pacing escape interval may be based on the onset of a sensed R-wave, a sensed P-wave, or other time point identified on the ECG signal.

If the pacing escape interval expires (block 808), a control signal is produced by the sensing device and sent to the optical emitting device 18 at block 810. The control signal produced by the sensing device may be an electrical signal sent to the emitting device 18 by an electrical conductor coupling the sensing device to the emitting device 18. As described above, the emitting device 18 may be housed within or along the housing of the sensing device or within a header or connector block of the sensing device. Alternatively the emitting device 18 may be carried by a lead coupled to the sensing device.

In other examples, the control signal produced by the sensing device is converted to a wireless telemetry communication signal that is transmitted to a receiver included in the emitting device. The emitting device 18 may be a leadless device implanted away from the sensing device or may be carried by a lead extending from the sensing device but configured to receive wireless telemetry signals, such as RF signals.

At block 812, the emitting device 18 generates an optical trigger signal upon receiving the control signal from the sensing device. An intracardiac pacemaker 100 is implanted in the LV and configured to detect the optical trigger signal as described above. If an optical trigger signal is detected by the pacemaker 100, as determined at block 814, the pacemaker 100 delivers an LV pacing pulse at block 816. If no optical trigger signal is detected, the sensing device continues to sense events from the ECG signal for controlling pacing timing intervals and generating control signals to cause triggered pacing pulse delivery by the pacemaker 100.

Thus, various examples of a medical device system including a triggered therapy delivery device and associated methods have been described according to illustrative embodiments. Various aspects of the examples presented herein may be combined in different combinations than the particular examples presented. One of ordinary skill in the art will appreciate that various modifications may be made to the described embodiments without departing from the scope of the following claims.

The invention claimed is:

1. A medical device system for automatically delivering a therapy, comprising:
    a first device configured to sense a physiological signal and generate a control signal in response to the physiological signal;
    an optical emitting device controlled by the first device to emit an optical trigger signal in response to receiving the control signal from the first device, wherein the optical trigger signal is not a physiological signal; and
    a second device comprising a light detector for receiving light incident on the second device and configured to detect the optical trigger signal emitted by the optical emitting device by producing a voltage signal in response to the light incident on the second device, comparing the voltage signal to a trigger detection threshold, and detecting the optical trigger signal in response to the voltage signal being greater than the trigger detection threshold, the second device configured to deliver a therapy to a patient in response to the light detector detecting the optical trigger signal.

2. The system of claim 1, wherein:
    the first device is configured to sense cardiac electrical signals via a plurality of electrodes coupled to the first device; and
    the second device is configured to deliver an electrical stimulation pulse to a targeted body tissue of the patient via a pair of electrodes coupled to the second device in response to detecting the optical trigger signal.

3. The system of claim 1, wherein the second device is wholly implantable within a heart chamber.

4. The system of claim 1, wherein the second device comprises a housing and an optical coupling window through the housing, the light detector comprising at least one photosensitive device mounted along an interior of the optical coupling window.

5. The system of claim 1, wherein the second device comprises an electrode coupled to the second device and an optical coupling window that is coaxial with the electrode, the light detector comprising at least one photosensitive device mounted along an interior of the optical coupling window.

6. The system of claim 5, wherein the second device comprises a housing and the optical coupling window is an insulating feedthrough member surrounding the electrode and extending through the housing.

7. The system of claim 1, wherein the optical emitting device is configured to emit the trigger signal having a signal bandwidth with a center wavelength at a local minima of an absorption spectra of a tissue pathway between the optical emitting device and the light detector.

8. The system of claim 1, wherein the optical emitting device is configured to emit the trigger signal having a center wavelength greater than 1000 nm.

9. The system of claim 1, wherein the optical emitting device is configured to emit the trigger signal comprising a wavelength of at least one of 1,100 nm, 1,300 nm, and 1,700 nm.

10. The system of claim 1, wherein the optical emitting device comprises a first optical transducer configured to emit a first wavelength and a second optical transducer configured to emit a second wavelength,
    the first device configured to selectively control the optical emitting device to emit the trigger signal as one of a first trigger signal having the first trigger signal wavelength and a second trigger signal having a second trigger signal wavelength;
    the second device light detector configured to detect the trigger signal as one of the first trigger signal and the second trigger signal and deliver a first therapy in response to detecting the first trigger signal and deliver a second therapy in response to detecting the second trigger signal.

11. The system of claim 1, wherein the optical emitting device is incorporated in the first device.

12. The system of claim 1, wherein the optical emitting device is a third device implantable at a spaced apart location from the first device and the second device, wherein the optical emitting device is configured to receive the control signal generated by the first device via one of a wired connection to the first device and a wireless communication signal from the first device.

13. The system of claim 1, wherein the second device further comprises:
    a pulse generator configured to generate electrical stimulation pulses;
    a control circuit coupled to the pulse generator and the light detector and configured to control the pulse generator to deliver an electrical stimulation pulse to a patient's heart in response to the light detector detecting the optical trigger signal;
    a power source comprising at least one battery supplying power to the pulse generator for generating the electrical stimulation pulses; and
    a housing enclosing the pulse generator, the light detector the control circuit and the power source.

14. A method for delivering an automatic therapy by a medical device system, comprising:
    sensing a physiological signal by a first device;
    generating a control signal by the first device in response to the physiological signal;
    controlling an optical emitting device to emit an optical trigger signal in response to the control signal, wherein the optical trigger signal is not a physiological signal;
    detecting the optical trigger signal by a second device comprising a light detector by:

receiving light incident on the second device by the light detector, producing a voltage signal in response to the light incident on the second device, comparing the voltage signal to a trigger detection threshold, and detecting the optical trigger signal in response to the voltage signal being greater than the trigger detection threshold; and delivering the therapy to a patient in response to the light detector detecting the optical trigger signal.

15. The method of claim 14, wherein the physiological signal is a cardiac signal sensed using a plurality of electrodes coupled to the first device,
wherein delivering the therapy in response to detecting the optical trigger signal comprises delivering an electrical stimulation pulse generated by the second device to a targeted body tissue of the patient using an electrode pair coupled to the second device.

16. The method of claim 14, further comprising transmitting the optical trigger signal from the optical emitting device to the second device wholly implanted within a heart chamber.

17. The method of claim 14, wherein detecting the optical trigger signal by the second device comprises receiving the optical trigger signal through an optical coupling window extending through a housing of the second device by at least one photosensitive device mounted along an interior of the optical coupling window.

18. The method of claim 14, wherein detecting the optical trigger signal by the second device comprises receiving the optical trigger signal through an optical coupling window that is coaxial with an electrode carried by the second device.

19. The method of claim 18, wherein receiving the optical trigger signal through the optical coupling window comprises receiving the optical trigger signal through an insulating feedthrough member surrounding the electrode.

20. The method of claim 14, further comprising emitting the trigger signal having a signal bandwidth with a center wavelength at a local minima of an absorption spectra of a tissue pathway between the optical emitting device and the light detector.

21. The method of claim 14, further comprising emitting the trigger signal having a center wavelength greater than 1000 nm.

22. The method of claim 14, wherein emitting the trigger signal comprises emitting a wavelength of at least one of 1,100 nm, 1,300 nm, and 1,700 nm.

23. The method of claim 14, further comprising:
selectively emitting the trigger signal as one of a first trigger signal having a first wavelength and a second trigger signal having a second wavelength;
detecting the trigger signal as one of the first trigger signal and the second trigger signal;
delivering a first therapy in response to detecting the first trigger signal and delivering a second therapy in response to detecting the second trigger signal.

24. A non-transitory computer readable storage medium storing a set of instructions that cause an implantable medical device system to:
sense a physiological signal by a first device;

generate a control signal by the first device in response to the physiological signal;
control an optical emitting device to emit an optical trigger signal in response to the control signal, wherein the optical trigger signal is not a physiological signal;
detect the optical trigger signal by a second device comprising a light detector by:
receiving light incident on the second device by the light detector, producing a voltage signal in response to the light incident on the second device, comparing the voltage signal to a trigger detection threshold, and detecting the optical trigger signal in response to the voltage signal being greater than the trigger detection threshold; and
deliver a therapy to a patient in response to the light detector detecting the optical trigger signal.

25. A medical device system for automatically delivering a therapy, comprising:
a first device configured to sense a physiological signal and generate a control signal in response to the physiological signal;
an optical emitting device controlled by the first device to emit an optical trigger signal in response to receiving the control signal from the first device; and
a second device comprising a light detector for receiving light incident on the second device and configured to detect the optical trigger signal emitted by the optical emitting device by producing a voltage signal in response to the light incident on the second device, comparing the voltage signal to a trigger detection threshold, and detecting the optical trigger signal in response to the voltage signal being greater than the trigger detection threshold, the second device configured to deliver a therapy to a patient in response to the light detector detecting the optical trigger signal;
wherein the second device further comprises:
a pulse generator configured to generate electrical stimulation pulses;
a control circuit coupled to the pulse generator and the light detector and configured to control the pulse generator to deliver an electrical stimulation pulse to a patient's heart in response to the light detector detecting the optical trigger signal;
a power source comprising at least one battery supplying power to the pulse generator for generating the electrical stimulation pulses; and
a housing enclosing the pulse generator, the light detector the control circuit and the power source
the light detector is configured to generate a trigger detect signal in response to detecting the optical trigger signal;
the pulse generator comprises a capacitor; and
the control circuit is configured to control the pulse generator to initiate charging of the pacing capacitor to a predetermined pacing pulse amplitude while waiting for the trigger detect signal.

* * * * *